(12) United States Patent
Battini et al.

(10) Patent No.: US 8,945,583 B2
(45) Date of Patent: Feb. 3, 2015

(54) GLUT-1 AS A RECEPTOR FOR HTLV ENVELOPES AND ITS USES

(75) Inventors: Jean-Luc Georges Laurent Battini, Montpellier (FR); Nicolas Gabriel Albert Manel, Montpellier (FR); Felix Jinhyun Kim, San Diego, CA (US); Sandrina Kinet, Montarnaud (FR); Naomi Taylor, Montpellier (FR); Marc Sitbon, Montpellier (FR)

(73) Assignees: Centre National de la Recherche Scientifique, Paris (FR); Universite de Montpellier 2, Montpellier (FR)

( * ) Notice: Subject to any disclaimer, the term of this patent is extended or adjusted under 35 U.S.C. 154(b) by 789 days.

(21) Appl. No.: 12/547,924

(22) Filed: Aug. 26, 2009

(65) Prior Publication Data
US 2010/0056448 A1 Mar. 4, 2010

Related U.S. Application Data

(62) Division of application No. 10/555,289, filed as application No. PCT/EP2004/004624 on Apr. 30, 2004, now Pat. No. 7,642,061.

(30) Foreign Application Priority Data

May 2, 2003 (EP) .................................. 03291067

(51) Int. Cl.
*A61K 38/16* (2006.01)
*A61P 35/00* (2006.01)
(Continued)

(52) U.S. Cl.
CPC ............ *G01N 33/566* (2013.01); *A61K 38/162* (2013.01); *C07K 14/005* (2013.01); *C07K 14/62* (2013.01); *C07K 14/705* (2013.01); *C12N 2740/15022* (2013.01); *C12N 2740/15045* (2013.01); *C12N 2810/6054* (2013.01)

USPC ................ 424/207.1; 424/187.1; 530/300; 530/350

(58) Field of Classification Search
None
See application file for complete search history.

(56) References Cited

U.S. PATENT DOCUMENTS

2010/0056448 A1* 3/2010 Battini et al. ................... 514/12

FOREIGN PATENT DOCUMENTS

| WO | WO 92/13946 | 8/1992 |
| WO | WO 96/41193 | 12/1996 |
| WO | WO 98/03197 | 1/1998 |

OTHER PUBLICATIONS

Buck et al. (European Journal of Nuclear Medicine and Molecular Imaging. 2004; (31, Supplement 1): S80-S87).*

(Continued)

*Primary Examiner* — Shanon A Foley
(74) *Attorney, Agent, or Firm* — Young & Thompson

(57) ABSTRACT

The invention relates to the use of the ubiquitous vertebrate glucose transporter GLUT1, or of fragments or sequences derived thereof, for the in vitro diagnosis of cancers, when used as a tumor marker, or for the screening of compounds useful for the preparation of drugs for the prevention or the treatment of pathologies linked to an infection of an individual with a PTLV, or pathologies linked to an overexpression of GLUT1 on cell surfaces, or the in vitro detection of GLUT1 on cell surfaces. The invention also relates to pharmaceutical compositions containing GLUT1, or fragments or sequences derived thereof, and to their uses such as in the frame of the prevention or the treatment of pathologies linked to an infection of an individual with a PTLV.

18 Claims, 13 Drawing Sheets

(51) Int. Cl.
  A61P 37/06    (2006.01)
  G01N 33/566   (2006.01)
  C07K 14/005   (2006.01)
  C07K 14/62    (2006.01)
  C07K 14/705   (2006.01)

(56) References Cited

OTHER PUBLICATIONS

Wood et al (British Journal of Nutrition 89:3-9, 2003).*
Vannucci et al (Glia 21:2-21, 1997).*
Brown (Journal of Inherited Metabolic Diseases 23:237-246, 2000).*
Young et al (American Journal of Cardiology 83:25H-30H, 1999).*
Ojeda et al. (American Journal of Physiology, Cell Physiology. 2012; 303: C530-C539).*
Koralnik et al. (Journal of Virology. 1994; 68 (4): 2693-2707).*
Mahieux et al. (Viruses. 2011; 3: 1074-1090).*
Jones et al. (Journal of Virology. 2009; 83 (10): 5244-5255).*
Harris D S et al: "Polarized Distribution of Glucose Transporter Isoforms in CACO-2 Cells", Proceedings of the National Academy of Sciences of the United States, vol. 89, No. 16, 1992, pp. 7556-7560, XP002254293, 1992 ISSN: 0027-8424, p. 7557, col. 1, line 4-line 11 p. 7557, col. 2, paragraph 2; figures 1, 3A, p. 7559, col. 2, last paragraph.

Mendez Luis E et al: "Expression of glucose transporter-1 in cervical cancer and its precursors." Gynecologic Oncology, vol. 86, No. 2, Aug. 2002, pp. 138-143, XP002254294 Aug. 2002, ISSN: 0090-8258 cited in the application, p. 140, col. 2, line 7—p. 141, col. 1, line 2; table 3, p. 142, col. 1, paragraph 1.
Lairmore M D et al: "Characterization of a B-Cell Immunodominant Epitope of Human T-Lymphotropic Virus Type 1 (HTLV-I) Envelope GP46" Cancer Letters, New York, NY, US, vol. 66, Sep. 14, 1992, pp. 11-20, XP000940582, ISSN: 0304-3835 abstract.
Tallet B et al: "Sequence variations in the amino- and carboxy-terminal parts of the surface envelope glycoprotein of HTLV type 1 induce specific neutralizing antibodies." Aids Research and Human Retroviruses. United States Mar. 1, 2001, vol. 17, No. 4, pp. 337-348, XP002254296 ISSN: 0889-2229, p. 346, col. 2, last paragraph, abstract.
Mueckler Mike et al: "Identification of an amino acid residue that lies between the exofacial vestibule and exofacial substrate-binding site of the Glut1 sugar permeation pathway." Journal of Biological Chemistry, vol. 272, No. 48, Nov. 28, 1997, pp. 30141-30146, XP002254295, ISSN: 0021-9258 cited in the application, figure 1.
Manel Nicolas et al: "GLUT-1 is the receptor of retrovirus HTLV!" Medecine Sciences: M/S. Mar. 2004, vol. 20, No. 3, Mar. 2004, pp. 277-279, XP002293056, ISSN: 0767-0974, the whole document.
Manel Nicolas et al: "The ubiquitous glucose transporter GLUT-1 is a receptor for HTLV." Cell, vol. 115, No. 4, Nov. 14, 2003, pp. 449-459, XP002293058, ISSN: 0092-8674, the whole document.

* cited by examiner

Figure 1 B

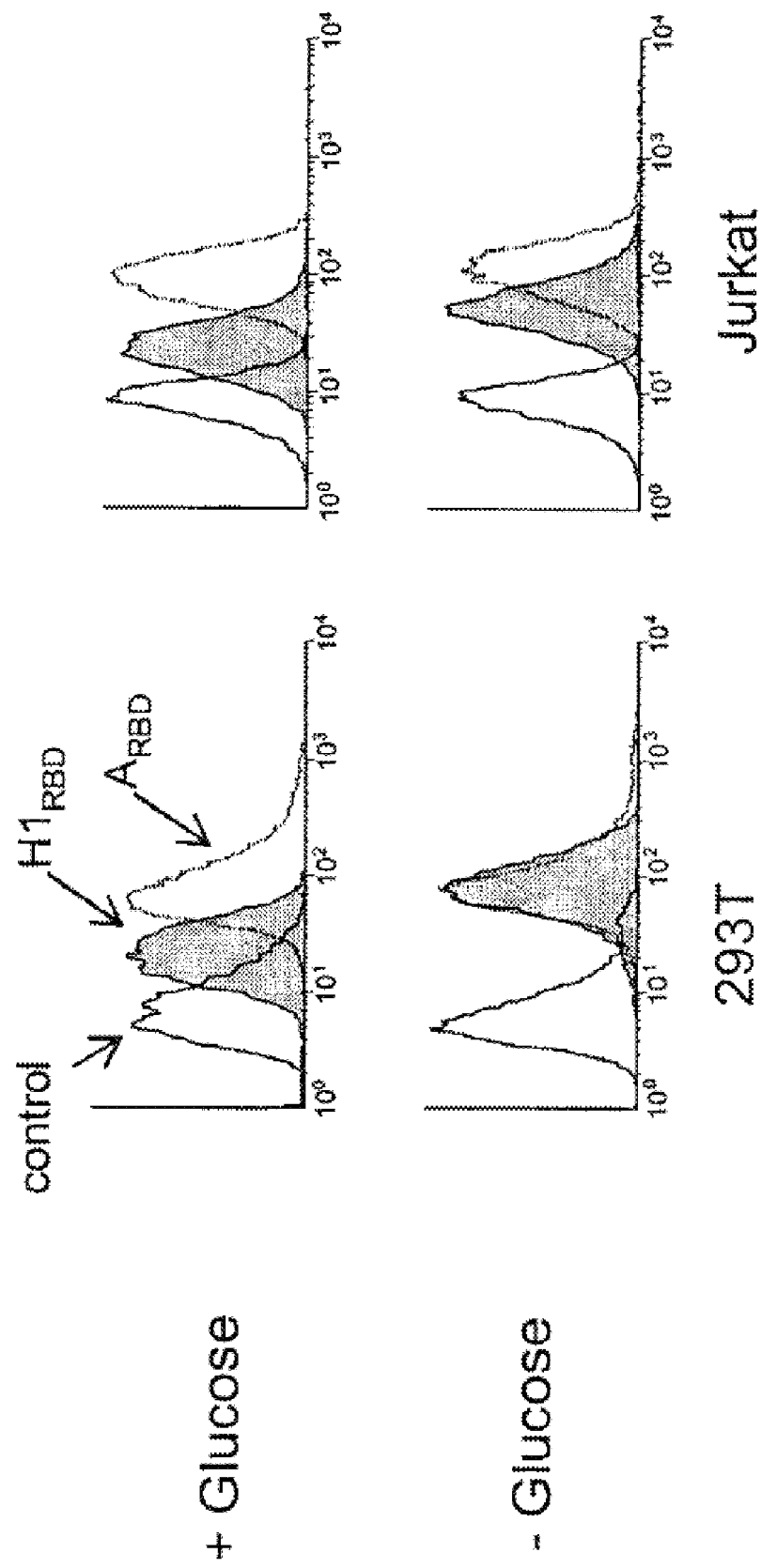

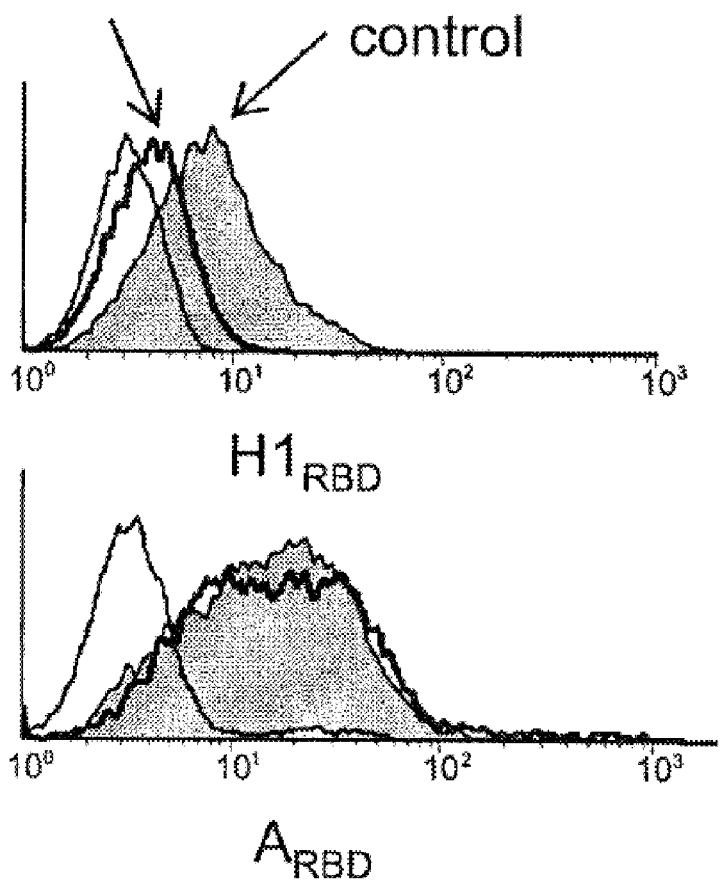

SEQUENCE LISTING

```
<160> NUMBER OF SEQ ID NOS: 32

<210> SEQ ID NO 1
<211> LENGTH: 1479
<212> TYPE: DNA
<213> ORGANISM: Homo sapiens
<220> FEATURE:
<221> NAME/KEY: CDS
<222> LOCATION: (1)..(1476)

<400> SEQUENCE: 1 atg gag ccc agc agc aag aag ctg acg ggt cgc ctc atg ctg gct gtg     48
Met Glu Pro Ser Ser Lys Lys Leu Thr Gly Arg Leu Met Leu Ala Val
 1               5                  10                  15 gga gga gca gtg ctt ggc tcc ctg cag ttt ggc tac aac act gga gtc     96
Gly Gly Ala Val Leu Gly Ser Leu Gln Phe Gly Tyr Asn Thr Gly Val
             20                  25                  30 atc aat gcc ccc cag aag gtg atc gag gag ttc tac aac cag aca tgg    144
Ile Asn Ala Pro Gln Lys Val Ile Glu Glu Phe Tyr Asn Gln Thr Trp
         35                  40                  45 gtc cac cgc tat ggg gag agc atc ctg ccc acc acg ctc acc acg ctc    192
Val His Arg Tyr Gly Glu Ser Ile Leu Pro Thr Thr Leu Thr Thr Leu
     50                  55                  60 tgg tcc ctc tca gtg gcc atc ttt tct gtt ggg ggc atg att ggc tcc    240
Trp Ser Leu Ser Val Ala Ile Phe Ser Val Gly Gly Met Ile Gly Ser
 65                  70                  75                  80
```

| | | |
|---|---|---|
| ttc tct gtg ggc ctt ttc gtt aac cgc ttt ggc cgg cgg aat tca atg<br>Phe Ser Val Gly Leu Phe Val Asn Arg Phe Gly Arg Arg Asn Ser Met<br>                 85                       90                       95 | 288 |
| ctg atg atg aac ctg ctg gcc ttc gtg tcc gcc gtg ctc atg ggc ttc<br>Leu Met Met Asn Leu Leu Ala Phe Val Ser Ala Val Leu Met Gly Phe<br>                100                     105                    110 | 336 |
| tcg aaa ctg ggc aag tcc ttt gag atg ctg atc ctg ggc cgc ttc atc<br>Ser Lys Leu Gly Lys Ser Phe Glu Met Leu Ile Leu Gly Arg Phe Ile<br>        115                     120                    125 | 384 |
| atc ggt gtg tac tgc ggc ctg acc aca ggc ttc gtg ccc atg tat gtg<br>Ile Gly Val Tyr Cys Gly Leu Thr Thr Gly Phe Val Pro Met Tyr Val<br>     130                    135                    140 | 432 |
| ggt gaa gtg tca ccc aca gcc ttt cgt ggg gcc ctg ggc acc ctg cac<br>Gly Glu Val Ser Pro Thr Ala Phe Arg Gly Ala Leu Gly Thr Leu His<br>145                   150                     155                   160 | 480 |
| cag ctg ggc atc gtc gtc ggc atc ctc atc gcc cag gtg ttc ggc ctg<br>Gln Leu Gly Ile Val Val Gly Ile Leu Ile Ala Gln Val Phe Gly Leu<br>                  165                     170                    175 | 528 |
| gac tcc atc atg ggc aac aag gac ctg tgg ccc ctg ctg agc atc<br>Asp Ser Ile Met Gly Asn Lys Asp Leu Trp Pro Leu Leu Ser Ile<br>              180                     185                    190 | 576 |
| atc ttc atc ccg gcc ctg ctg cag tgc atc gtg ctg ccc ttc tgc ccc<br>Ile Phe Ile Pro Ala Leu Leu Gln Cys Ile Val Leu Pro Phe Cys Pro<br>        195                     200                    205 | 624 |
| gag agt ccc cgc ttc ctg ctc atc aac cgc aac gag gag aac cgg gcc<br>Glu Ser Pro Arg Phe Leu Leu Ile Asn Arg Asn Glu Glu Asn Arg Ala<br>     210                    215                    220 | 672 |
| aag agt gtg cta aag aag ctg cgc ggg aca gct gac gtg acc cat gac<br>Lys Ser Val Leu Lys Lys Leu Arg Gly Thr Ala Asp Val Thr His Asp<br>225                   230                     235                   240 | 720 |
| ctg cag gag atg aag gaa gag agt cgg cag atg atg cgg gag aag aag<br>Leu Gln Glu Met Lys Glu Glu Ser Arg Gln Met Met Arg Glu Lys Lys<br>                      245                     250                    255 | 768 |
| gtc acc atc ctg gag ctg ttc cgc tcc ccc gcc tac cgc cag ccc atc<br>Val Thr Ile Leu Glu Leu Phe Arg Ser Pro Ala Tyr Arg Gln Pro Ile<br>                  260                     265                    270 | 816 |
| ctc atc gct gtg gtg ctg cag ctg tcc cag cag ctg tct ggc atc aac<br>Leu Ile Ala Val Val Leu Gln Leu Ser Gln Gln Leu Ser Gly Ile Asn<br>     275                    280                    285 | 864 |
| gct gtc ttc tat tac tcc acg agc atc ttc gag aag gcg ggg gtg cag<br>Ala Val Phe Tyr Tyr Ser Thr Ser Ile Phe Glu Lys Ala Gly Val Gln<br>        290                     295                    300 | 912 |
| cag cct gtg tat gcc acc att ggc tcc ggt atc gtc aac acg gcc ttc<br>Gln Pro Val Tyr Ala Thr Ile Gly Ser Gly Ile Val Asn Thr Ala Phe<br>305                   310                     315                   320 | 960 |
| act gtc gtg tcg ctg ttt gtg gtg gag cga gca ggc cgg cgg acc ctg<br>Thr Val Val Ser Leu Phe Val Val Glu Arg Ala Gly Arg Arg Thr Leu<br>                  325                     330                    335 | 1008 |
| cac ctc ata ggc ctc gct ggc atg gcg ggt tgt gcc ata ctc atg acc<br>His Leu Ile Gly Leu Ala Gly Met Ala Gly Cys Ala Ile Leu Met Thr<br>                   340                    345                   350 | 1056 |
| atc gcg cta gca ctg ctg gag cag cta ccc tgg atg tcc tat ctg agc<br>Ile Ala Leu Ala Leu Leu Glu Gln Leu Pro Trp Met Ser Tyr Leu Ser<br>        355                     360                    365 | 1104 |
| atc gtg gcc atc ttt ggc ttt gtg gcc ttc ttt gaa gtg ggt cct ggc<br>Ile Val Ala Ile Phe Gly Phe Val Ala Phe Phe Glu Val Gly Pro Gly<br>     370                    375                    380 | 1152 |
| ccc atc cca tgg ttc atc gtg gct gaa ctc ttc agc cag ggt cca cgt<br>Pro Ile Pro Trp Phe Ile Val Ala Glu Leu Phe Ser Gln Gly Pro Arg<br>385                   390                     395                   400 | 1200 |

-continued

```
cca gct gcc att gcc gtt gca ggc ttc tcc aac tgg acc tca aat ttc    1248
Pro Ala Ala Ile Ala Val Ala Gly Phe Ser Asn Trp Thr Ser Asn Phe
            405                 410                 415 att gtg ggc atg tgc ttc cag tat gtg gag caa ctg tgt ggt ccc tac    1296
Ile Val Gly Met Cys Phe Gln Tyr Val Glu Gln Leu Cys Gly Pro Tyr
            420                 425                 430 gtc ttc atc atc ttc act gtg ctc ctg gtt ctg ttc ttc atc ttc acc    1344
Val Phe Ile Ile Phe Thr Val Leu Leu Val Leu Phe Phe Ile Phe Thr
            435                 440                 445 tac ttc aaa gtt cct gag act aaa ggc cgg acc ttc gat gag atc gct    1392
Tyr Phe Lys Val Pro Glu Thr Lys Gly Arg Thr Phe Asp Glu Ile Ala
    450                 455                 460 tcc ggc ttc cgg cag ggg gga gcc agc caa agt gat aag aca ccc gag    1440
Ser Gly Phe Arg Gln Gly Gly Ala Ser Gln Ser Asp Lys Thr Pro Glu
465                 470                 475                 480 gag ctg ttc cat ccc ctg ggg gct gat tcc caa gtg tga                1479
Glu Leu Phe His Pro Leu Gly Ala Asp Ser Gln Val
                    485                 490
```

<210> SEQ ID NO 2
<211> LENGTH: 492
<212> TYPE: PRT
<213> ORGANISM: Homo sapiens

<400> SEQUENCE: 2

```
Met Glu Pro Ser Ser Lys Lys Leu Thr Gly Arg Leu Met Leu Ala Val
 1               5                  10                  15

Gly Gly Ala Val Leu Gly Ser Leu Gln Phe Gly Tyr Asn Thr Gly Val
            20                  25                  30

Ile Asn Ala Pro Gln Lys Val Ile Glu Glu Phe Tyr Asn Gln Thr Trp
        35                  40                  45

Val His Arg Tyr Gly Glu Ser Ile Leu Pro Thr Thr Leu Thr Thr Leu
    50                  55                  60

Trp Ser Leu Ser Val Ala Ile Phe Ser Val Gly Gly Met Ile Gly Ser
65                  70                  75                  80

Phe Ser Val Gly Leu Phe Val Asn Arg Phe Gly Arg Arg Asn Ser Met
                85                  90                  95

Leu Met Met Asn Leu Leu Ala Phe Val Ser Ala Val Leu Met Gly Phe
            100                 105                 110

Ser Lys Leu Gly Lys Ser Phe Glu Met Leu Ile Leu Gly Arg Phe Ile
        115                 120                 125

Ile Gly Val Tyr Cys Gly Leu Thr Thr Gly Phe Val Pro Met Tyr Val
    130                 135                 140

Gly Glu Val Ser Pro Thr Ala Phe Arg Gly Ala Leu Gly Thr Leu His
145                 150                 155                 160

Gln Leu Gly Ile Val Val Gly Ile Leu Ile Ala Gln Val Phe Gly Leu
                165                 170                 175

Asp Ser Ile Met Gly Asn Lys Asp Leu Trp Pro Leu Leu Leu Ser Ile
            180                 185                 190

Ile Phe Ile Pro Ala Leu Leu Gln Cys Ile Val Leu Pro Phe Cys Pro
        195                 200                 205

Glu Ser Pro Arg Phe Leu Leu Ile Asn Arg Asn Glu Glu Asn Arg Ala
    210                 215                 220

Lys Ser Val Leu Lys Lys Leu Arg Gly Thr Ala Asp Val Thr His Asp
225                 230                 235                 240

Leu Gln Glu Met Lys Glu Glu Ser Arg Gln Met Met Arg Glu Lys Lys
```

```
                     245                 250                 255
Val Thr Ile Leu Glu Leu Phe Arg Ser Pro Ala Tyr Arg Gln Pro Ile
            260                 265                 270

Leu Ile Ala Val Val Leu Gln Leu Ser Gln Gln Leu Ser Gly Ile Asn
        275                 280                 285

Ala Val Phe Tyr Tyr Ser Thr Ser Ile Phe Glu Lys Ala Gly Val Gln
        290                 295                 300

Gln Pro Val Tyr Ala Thr Ile Gly Ser Gly Ile Val Asn Thr Ala Phe
305                 310                 315                 320

Thr Val Val Ser Leu Phe Val Val Glu Arg Ala Gly Arg Arg Thr Leu
                325                 330                 335

His Leu Ile Gly Leu Ala Gly Met Ala Gly Cys Ala Ile Leu Met Thr
            340                 345                 350

Ile Ala Leu Ala Leu Leu Glu Gln Leu Pro Trp Met Ser Tyr Leu Ser
        355                 360                 365

Ile Val Ala Ile Phe Gly Phe Val Ala Phe Phe Glu Val Gly Pro Gly
        370                 375                 380

Pro Ile Pro Trp Phe Ile Val Ala Glu Leu Phe Ser Gln Gly Pro Arg
385                 390                 395                 400

Pro Ala Ala Ile Ala Val Ala Gly Phe Ser Asn Trp Thr Ser Asn Phe
                405                 410                 415

Ile Val Gly Met Cys Phe Gln Tyr Val Glu Gln Leu Cys Gly Pro Tyr
            420                 425                 430

Val Phe Ile Ile Phe Thr Val Leu Leu Val Leu Phe Phe Ile Phe Thr
        435                 440                 445

Tyr Phe Lys Val Pro Glu Thr Lys Gly Arg Thr Phe Asp Glu Ile Ala
        450                 455                 460

Ser Gly Phe Arg Gln Gly Gly Ala Ser Gln Ser Asp Lys Thr Pro Glu
465                 470                 475                 480

Glu Leu Phe His Pro Leu Gly Ala Asp Ser Gln Val
                485                 490

<210> SEQ ID NO 3
<211> LENGTH: 924
<212> TYPE: DNA
<213> ORGANISM: Human T-cell lymphotropic virus type 1
<220> FEATURE:
<221> NAME/KEY: CDS
<222> LOCATION: (1)..(924)

<400> SEQUENCE: 3 atg ggt aag ttt ctc gcc act ttg att tta ttc ttc cag ttc tgc ccc      48
Met Gly Lys Phe Leu Ala Thr Leu Ile Leu Phe Phe Gln Phe Cys Pro
  1               5                  10                  15 ctc atc ctc ggt gat tac agc ccc agc tgc tgt act ctc aca att gga      96
Leu Ile Leu Gly Asp Tyr Ser Pro Ser Cys Cys Thr Leu Thr Ile Gly
             20                  25                  30 gtc tcc tca tac cac tct aaa ccc tgc aat cct gcc cag cca gtt tgt     144
Val Ser Ser Tyr His Ser Lys Pro Cys Asn Pro Ala Gln Pro Val Cys
         35                  40                  45 tcg tgg acc ctc gac ctg ctg gcc ctt tca gcg gat cag gcc cta cag     192
Ser Trp Thr Leu Asp Leu Leu Ala Leu Ser Ala Asp Gln Ala Leu Gln
     50                  55                  60 ccc ccc tgc cct aat cta gta agt tac tcc agc tac cat gcc acc tat     240
Pro Pro Cys Pro Asn Leu Val Ser Tyr Ser Ser Tyr His Ala Thr Tyr
 65                  70                  75                  80 tcc cta tat cta ttc cct cat tgg att aaa aag cca aac cga aat ggc     288
```

```
                Ser Leu Tyr Leu Phe Pro His Trp Ile Lys Lys Pro Asn Arg Asn Gly
                                85                  90                  95 gga ggc tat tat tca gcc tct tat tca gac cct tgt tcc tta aag tgc          336
Gly Gly Tyr Tyr Ser Ala Ser Tyr Ser Asp Pro Cys Ser Leu Lys Cys
            100                 105                 110 cca tac ctg ggg tgc caa tca tgg acc tgc ccc tat aca gga gcc gtc          384
Pro Tyr Leu Gly Cys Gln Ser Trp Thr Cys Pro Tyr Thr Gly Ala Val
            115                 120                 125 tcc agc ccc tac tgg aag ttt cag caa gat gtc aat ttt act caa gaa          432
Ser Ser Pro Tyr Trp Lys Phe Gln Gln Asp Val Asn Phe Thr Gln Glu
        130                 135                 140 gtt tca cgc ctc aat att aat ctc cat ttt tca aaa tgc ggt ttt ccc          480
Val Ser Arg Leu Asn Ile Asn Leu His Phe Ser Lys Cys Gly Phe Pro
145                 150                 155                 160 ttc tcc ctt cta gtc gac gct cca gga tat gac ccc atc tgg ttc ctt          528
Phe Ser Leu Leu Val Asp Ala Pro Gly Tyr Asp Pro Ile Trp Phe Leu
                165                 170                 175 aat acc gaa ccc agc caa ctg cct ccc acc gcc cct cct cta ctc ccc          576
Asn Thr Glu Pro Ser Gln Leu Pro Pro Thr Ala Pro Pro Leu Leu Pro
            180                 185                 190 cac tct aac cta gac cac atc ctc gag ccc tct ata cca tgg aaa tca          624
His Ser Asn Leu Asp His Ile Leu Glu Pro Ser Ile Pro Trp Lys Ser
        195                 200                 205 aaa ctc ctg acc ctt gtc cag tta acc cta caa agc act aat tat act          672
Lys Leu Leu Thr Leu Val Gln Leu Thr Leu Gln Ser Thr Asn Tyr Thr
    210                 215                 220 tgc att gtc tgt atc gat cgt gcc agc cta tcc act tgg cac gtc cta          720
Cys Ile Val Cys Ile Asp Arg Ala Ser Leu Ser Thr Trp His Val Leu
225                 230                 235                 240 tac tct ccc aac gtc tct gtt cca tcc tct tct tct acc ccc ctc ctt          768
Tyr Ser Pro Asn Val Ser Val Pro Ser Ser Ser Ser Thr Pro Leu Leu
                245                 250                 255 tac cca tcg tta gcg ctt cca gcc ccc cac ctg acg tta cca ttt aac          816
Tyr Pro Ser Leu Ala Leu Pro Ala Pro His Leu Thr Leu Pro Phe Asn
            260                 265                 270 tgg acc cac tgc ttt gac ccc cag att caa gct ata gtc tcc tcc ccc          864
Trp Thr His Cys Phe Asp Pro Gln Ile Gln Ala Ile Val Ser Ser Pro
        275                 280                 285 tgt cat aac tcc ctc atc ctg ccc ccc ttt tcc ttg tca cct gtt ccc          912
Cys His Asn Ser Leu Ile Leu Pro Pro Phe Ser Leu Ser Pro Val Pro
    290                 295                 300 acc cta gga tcc                                                          924
Thr Leu Gly Ser
305

<210> SEQ ID NO 4
<211> LENGTH: 308
<212> TYPE: PRT
<213> ORGANISM: Human T-cell lymphotropic virus type 1

<400> SEQUENCE: 4

Met Gly Lys Phe Leu Ala Thr Leu Ile Leu Phe Phe Gln Phe Cys Pro
 1               5                  10                  15

Leu Ile Leu Gly Asp Tyr Ser Pro Ser Cys Cys Thr Leu Thr Ile Gly
                20                  25                  30

Val Ser Ser Tyr His Ser Lys Pro Cys Asn Pro Ala Gln Pro Val Cys
            35                  40                  45

Ser Trp Thr Leu Asp Leu Leu Ala Leu Ser Ala Asp Gln Ala Leu Gln
        50                  55                  60
```

```
Pro Pro Cys Pro Asn Leu Val Ser Tyr Ser Ser Tyr His Ala Thr Tyr
 65                  70                  75                  80

Ser Leu Tyr Leu Phe Pro His Trp Ile Lys Lys Pro Asn Arg Asn Gly
                 85                  90                  95

Gly Gly Tyr Tyr Ser Ala Ser Tyr Ser Asp Pro Cys Ser Leu Lys Cys
            100                 105                 110

Pro Tyr Leu Gly Cys Gln Ser Trp Thr Cys Pro Tyr Thr Gly Ala Val
            115                 120                 125

Ser Ser Pro Tyr Trp Lys Phe Gln Gln Asp Val Asn Phe Thr Gln Glu
        130                 135                 140

Val Ser Arg Leu Asn Ile Asn Leu His Phe Ser Lys Cys Gly Phe Pro
145                 150                 155                 160

Phe Ser Leu Leu Val Asp Ala Pro Gly Tyr Asp Pro Ile Trp Phe Leu
                165                 170                 175

Asn Thr Glu Pro Ser Gln Leu Pro Pro Thr Ala Pro Pro Leu Leu Pro
            180                 185                 190

His Ser Asn Leu Asp His Ile Leu Glu Pro Ser Ile Pro Trp Lys Ser
        195                 200                 205

Lys Leu Leu Thr Leu Val Gln Leu Thr Leu Gln Ser Thr Asn Tyr Thr
    210                 215                 220

Cys Ile Val Cys Ile Asp Arg Ala Ser Leu Ser Thr Trp His Val Leu
225                 230                 235                 240

Tyr Ser Pro Asn Val Ser Val Pro Ser Ser Ser Thr Pro Leu Leu
                245                 250                 255

Tyr Pro Ser Leu Ala Leu Pro Ala Pro His Leu Thr Leu Pro Phe Asn
            260                 265                 270

Trp Thr His Cys Phe Asp Pro Gln Ile Gln Ala Ile Val Ser Ser Pro
        275                 280                 285

Cys His Asn Ser Leu Ile Leu Pro Pro Phe Ser Leu Ser Pro Val Pro
    290                 295                 300

Thr Leu Gly Ser
305

<210> SEQ ID NO 5
<211> LENGTH: 912
<212> TYPE: DNA
<213> ORGANISM: Human T-cell lymphotropic virus type 2
<220> FEATURE:
<221> NAME/KEY: CDS
<222> LOCATION: (1)..(912)

<400> SEQUENCE: 5 atg ggt aac gtt ttc ttc cta ctt tta ttc agt ctc aca cac ttc cca      48
Met Gly Asn Val Phe Phe Leu Leu Leu Phe Ser Leu Thr His Phe Pro
  1               5                  10                  15 cca gtc cag cag agc cga tgc aca ctc acg gtt ggt att tcc tcc tac      96
Pro Val Gln Gln Ser Arg Cys Thr Leu Thr Val Gly Ile Ser Ser Tyr
             20                  25                  30 cac tcc agc ccc tgt agc cca acc caa ccc gtc tgc acg tgg aac ctc     144
His Ser Ser Pro Cys Ser Pro Thr Gln Pro Val Cys Thr Trp Asn Leu
         35                  40                  45 gac ctt aat tcc cta acg acg gac cag cga cta cat ccc ccc tgc cct     192
Asp Leu Asn Ser Leu Thr Thr Asp Gln Arg Leu His Pro Pro Cys Pro
     50                  55                  60 aac cta att act tac tct ggc ttc cac aaa act tat tcc tta tac tta     240
Asn Leu Ile Thr Tyr Ser Gly Phe His Lys Thr Tyr Ser Leu Tyr Leu
 65                  70                  75                  80
```

| | | |
|---|---|---|
| ttc cca cat tgg ata aag aag cca aat aga cag ggc cta gga tac tac<br>Phe Pro His Trp Ile Lys Lys Pro Asn Arg Gln Gly Leu Gly Tyr Tyr<br>                85                      90                  95 | 288 |
| tcg ccc tcc tat aat gac cct tgc tcg cta caa tgc ccc tac tta ggc<br>Ser Pro Ser Tyr Asn Asp Pro Cys Ser Leu Gln Cys Pro Tyr Leu Gly<br>                100               105             110 | 336 |
| tgc caa tca tgg aca tgc cca tac acg ggc ccc gtc tcc agt cca tcc<br>Cys Gln Ser Trp Thr Cys Pro Tyr Thr Gly Pro Val Ser Ser Pro Ser<br>              115                  120              125 | 384 |
| tgg aag ttt cac tca gat gta aat ttc acc caa gaa gtc agc caa gtg<br>Trp Lys Phe His Ser Asp Val Asn Phe Thr Gln Glu Val Ser Gln Val<br>130                 135               140 | 432 |
| tcc ctt cga cta cac ttc tct aag tgc ggc tcc tcc atg acc ctt cta<br>Ser Leu Arg Leu His Phe Ser Lys Cys Gly Ser Ser Met Thr Leu Leu<br>145                 150               155             160 | 480 |
| gta gat gcc cct gga tat gat cct tta tgg ttc atc acc tca gaa ccc<br>Val Asp Ala Pro Gly Tyr Asp Pro Leu Trp Phe Ile Thr Ser Glu Pro<br>                        165               170              175 | 528 |
| act cag cct ccc cca act cct ccc cca ctg gtc cat gac tcc gac ctt<br>Thr Gln Pro Pro Pro Thr Pro Pro Pro Leu Val His Asp Ser Asp Leu<br>                180                  185              190 | 576 |
| gaa cac gtc cta acc ccc tcc acg tct tgg aca acc aaa atg ctc aag<br>Glu His Val Leu Thr Pro Ser Thr Ser Trp Thr Thr Lys Met Leu Lys<br>             195                 200              205 | 624 |
| ttt atc cag ctg acc ttg cag agc acc aat tac tcc tgc atg gtt tgc<br>Phe Ile Gln Leu Thr Leu Gln Ser Thr Asn Tyr Ser Cys Met Val Cys<br>210                 215               220 | 672 |
| gtg gat aga tcc agc ctc tca tcc tgg cat gtg ctc tac acc ccc aac<br>Val Asp Arg Ser Ser Leu Ser Ser Trp His Val Leu Tyr Thr Pro Asn<br>225                 230               235             240 | 720 |
| atc tcc att ccc caa caa acc tcc tcc cga acc atc ctc ttt cct tct<br>Ile Ser Ile Pro Gln Gln Thr Ser Ser Arg Thr Ile Leu Phe Pro Ser<br>                        245               250              255 | 768 |
| ctt gcc ctg ccc gct cct cca ttc caa ccc ttc cct tgg acc cat tgc<br>Leu Ala Leu Pro Ala Pro Pro Phe Gln Pro Phe Pro Trp Thr His Cys<br>                260                  265              270 | 816 |
| tac caa cct cgc cta cag gca ata acg aca gat gac tgc aac aac tcc<br>Tyr Gln Pro Arg Leu Gln Ala Ile Thr Thr Asp Asp Cys Asn Asn Ser<br>             275                 280              285 | 864 |
| att atc ctc ccc cct ttt tcc ctc gcc ccc gta cct cct ccg gcg aca<br>Ile Ile Leu Pro Pro Phe Ser Leu Ala Pro Val Pro Pro Pro Ala Thr<br>          290                 295              300 | 912 |

<210> SEQ ID NO 6
<211> LENGTH: 304
<212> TYPE: PRT
<213> ORGANISM: Human T-cell lymphotropic virus type 2

<400> SEQUENCE: 6

Met Gly Asn Val Phe Phe Leu Leu Leu Phe Ser Leu Thr His Phe Pro
1                  5                    10                  15

Pro Val Gln Gln Ser Arg Cys Thr Leu Thr Val Gly Ile Ser Ser Tyr
                 20                    25                    30

His Ser Ser Pro Cys Ser Pro Thr Gln Pro Val Cys Thr Trp Asn Leu
                35                  40                   45

Asp Leu Asn Ser Leu Thr Thr Asp Gln Arg Leu His Pro Pro Cys Pro
     50                  55                  60

Asn Leu Ile Thr Tyr Ser Gly Phe His Lys Thr Tyr Ser Leu Tyr Leu
65                  70                   75                 80

-continued

```
Phe Pro His Trp Ile Lys Lys Pro Asn Arg Gln Gly Leu Gly Tyr Tyr
                85                  90                  95

Ser Pro Ser Tyr Asn Asp Pro Cys Ser Leu Gln Cys Pro Tyr Leu Gly
            100                 105                 110

Cys Gln Ser Trp Thr Cys Pro Tyr Thr Gly Pro Val Ser Ser Pro Ser
        115                 120                 125

Trp Lys Phe His Ser Asp Val Asn Phe Thr Gln Glu Val Ser Gln Val
    130                 135                 140

Ser Leu Arg Leu His Phe Ser Lys Cys Gly Ser Ser Met Thr Leu Leu
145                 150                 155                 160

Val Asp Ala Pro Gly Tyr Asp Pro Leu Trp Phe Ile Thr Ser Glu Pro
                165                 170                 175

Thr Gln Pro Pro Thr Pro Pro Leu Val His Asp Ser Asp Leu
            180                 185                 190

Glu His Val Leu Thr Pro Ser Thr Ser Trp Thr Thr Lys Met Leu Lys
        195                 200                 205

Phe Ile Gln Leu Thr Leu Gln Ser Thr Asn Tyr Ser Cys Met Val Cys
    210                 215                 220

Val Asp Arg Ser Ser Leu Ser Ser Trp His Val Leu Tyr Thr Pro Asn
225                 230                 235                 240

Ile Ser Ile Pro Gln Gln Thr Ser Ser Arg Thr Ile Leu Phe Pro Ser
                245                 250                 255

Leu Ala Leu Pro Ala Pro Pro Phe Gln Pro Phe Pro Trp Thr His Cys
            260                 265                 270

Tyr Gln Pro Arg Leu Gln Ala Ile Thr Thr Asp Asp Cys Asn Asn Ser
        275                 280                 285

Ile Ile Leu Pro Pro Phe Ser Leu Ala Pro Val Pro Pro Ala Thr
    290                 295                 300

<210> SEQ ID NO 7
<211> LENGTH: 1467
<212> TYPE: DNA
<213> ORGANISM: Simian T-cell lymphotropic virus type 1
<220> FEATURE:
<221> NAME/KEY: CDS
<222> LOCATION: (1)..(1465)

<400> SEQUENCE: 7 atg ggt aag ttt ctc gcc act ttg att tta ttc ttc cag ttc tgc ccc      48
Met Gly Lys Phe Leu Ala Thr Leu Ile Leu Phe Phe Gln Phe Cys Pro
 1               5                  10                  15 ctc att ctc ggt gat tac agc ccc agc tgc tgt act ctc aca att gga     96
Leu Ile Leu Gly Asp Tyr Ser Pro Ser Cys Cys Thr Leu Thr Ile Gly
            20                  25                  30 gtc tcc tca tac ctc tct aaa ccc tgc aat cct gcc agc cag ttg tgt    144
Val Ser Ser Tyr Leu Ser Lys Pro Cys Asn Pro Ala Gln Pro Val Cys
        35                  40                  45 tca tgg acc ctc gac cta ctg gcc ctt tca gca gac caa gcc cta cag    192
Ser Trp Thr Leu Asp Leu Leu Ala Leu Ser Ala Asp Gln Ala Leu Gln
    50                  55                  60 ccc ccc tgc cct aat cta gta agt tac tcc agc tac cat gcc acc tat    240
Pro Pro Cys Pro Asn Leu Val Ser Tyr Ser Ser Tyr His Ala Thr Tyr
65                  70                  75                  80 tcc cta tat cta ttc cct cat tgg att aaa aag cca aac cga aat ggc    288
Ser Leu Tyr Leu Phe Pro His Trp Ile Lys Lys Pro Asn Arg Asn Gly
                85                  90                  95 gga ggc tat tat tcg gcc tct tat tca gac cca tgt tct tta aag tgc    336
Gly Gly Tyr Tyr Ser Ala Ser Tyr Ser Asp Pro Cys Ser Leu Lys Cys
```

```
                100                   105                    110
cca tac tta ggg tgc caa tca tgg acc tgc ccc tat aca gga gtc gtc      384
Pro Tyr Leu Gly Cys Gln Ser Trp Thr Cys Pro Tyr Thr Gly Val Val
        115                   120                   125 tcc agc ccc tat tgg aaa ttt cag caa gat gtc aat ttt act caa gaa      432
Ser Ser Pro Tyr Trp Lys Phe Gln Gln Asp Val Asn Phe Thr Gln Glu
    130                   135                   140 gtt tca cac ctc aat att aat ctc cat ttc tca aaa tgc ggt ttt ccc      480
Val Ser His Leu Asn Ile Asn Leu His Phe Ser Lys Cys Gly Phe Pro
145                   150                   155                   160 ttc tcc ctt cta atc gac gct cca gga tat gac ccc atc tgg ttc ctt      528
Phe Ser Leu Leu Ile Asp Ala Pro Gly Tyr Asp Pro Ile Trp Phe Leu
                165                   170                   175 aat acc gaa ccc agc caa ctg cct ccc acc gcc cct cct cta ctc ccc      576
Asn Thr Glu Pro Ser Gln Leu Pro Pro Thr Ala Pro Pro Leu Leu Pro
            180                   185                   190 cac tct aac ctg gac cac atc ctc gag ccc tct ata cca tgg aaa tca      624
His Ser Asn Leu Asp His Ile Leu Glu Pro Ser Ile Pro Trp Lys Ser
        195                   200                   205 aaa ctt ctg act ctt gtc cag cta acc cta caa agc act aat tac act      672
Lys Leu Leu Thr Leu Val Gln Leu Thr Leu Gln Ser Thr Asn Tyr Thr
    210                   215                   220 tgc atc gtc tgt ata gac cgt gcc agc ctc tct act tgg cat gtc ctg      720
Cys Ile Val Cys Ile Asp Arg Ala Ser Leu Ser Thr Trp His Val Leu
225                   230                   235                   240 tac tct ccc aac gtc tct gtt ccg tcc tct tct tct acc ccc ctc ctt      768
Tyr Ser Pro Asn Val Ser Val Pro Ser Ser Ser Ser Thr Pro Leu Leu
                245                   250                   255 tac ccg tcg tta gcg ctt cca gct ccc cac ctg acg cta cca ttt aac      816
Tyr Pro Ser Leu Ala Leu Pro Ala Pro His Leu Thr Leu Pro Phe Asn
            260                   265                   270 tgg acc cac tgc ttt gac ccc cag att caa gct ata gtc tcc tcc ccc      864
Trp Thr His Cys Phe Asp Pro Gln Ile Gln Ala Ile Val Ser Ser Pro
        275                   280                   285 tgt cat aac tcc ctc atc ctg ccc ccc ttt tcc ttg tca cct gtt ccc      912
Cys His Asn Ser Leu Ile Leu Pro Pro Phe Ser Leu Ser Pro Val Pro
    290                   295                   300 acc cta gga tcc cgc tcc cgc cga gcg gta ccg gtg gcg gtc tgg ctt      960
Thr Leu Gly Ser Arg Ser Arg Arg Ala Val Pro Val Ala Val Trp Leu
305                   310                   315                   320 gtc tcc gcc ctg gcc atg gga gcc gga att gct ggc ggg att acc ggc     1008
Val Ser Ala Leu Ala Met Gly Ala Gly Ile Ala Gly Gly Ile Thr Gly
                325                   330                   335 tcc atg tcc ctc gcc tca gga aag agc ctc cta cat gag gtg gac aaa     1056
Ser Met Ser Leu Ala Ser Gly Lys Ser Leu Leu His Glu Val Asp Lys
            340                   345                   350 gat att tcc caa tta act caa gca ata gtc aaa aac cac aaa aat cta     1104
Asp Ile Ser Gln Leu Thr Gln Ala Ile Val Lys Asn His Lys Asn Leu
        355                   360                   365 ctc aaa att gca cag tat gct gcc cag aac agg cga ggc ctt gat ctc     1152
Leu Lys Ile Ala Gln Tyr Ala Ala Gln Asn Arg Arg Gly Leu Asp Leu
    370                   375                   380 ctg ttc tgg gag caa gga gga tta tgc aaa gca tta caa gaa cag tgc     1200
Leu Phe Trp Glu Gln Gly Gly Leu Cys Lys Ala Leu Gln Glu Gln Cys
385                   390                   395                   400 tgt ttt cta aat att acc aat tcc cat gtc tca ata cta caa gaa aga     1248
Cys Phe Leu Asn Ile Thr Asn Ser His Val Ser Ile Leu Gln Glu Arg
                405                   410                   415 ccc ccc ctt gag aat cga gtc ctc act ggc tgg ggc ctt aac tgg gac     1296
```

```
Pro Pro Leu Glu Asn Arg Val Leu Thr Gly Trp Gly Leu Asn Trp Asp
                420                 425                 430 ctt ggc ctc tca cag tgg gct cga gag gcc tta caa act ggg atc acc    1344
Leu Gly Leu Ser Gln Trp Ala Arg Glu Ala Leu Gln Thr Gly Ile Thr
            435                 440                 445 ctt gtt gca cta ctc ctt ctc gtt atc ctt gca gga cca tgc atc ctc    1392
Leu Val Ala Leu Leu Leu Leu Val Ile Leu Ala Gly Pro Cys Ile Leu
        450                 455                 460 cgt cag ctg cga cac ctc ccc tcg cgc gtc aga tac ccc cat tat tct    1440
Arg Gln Leu Arg His Leu Pro Ser Arg Val Arg Tyr Pro His Tyr Ser
465                 470                 475                 480 ctt ata aac cct gag tca tcc ctg taa                                1467
Leu Ile Asn Pro Glu Ser Ser Leu
                485

<210> SEQ ID NO 8
<211> LENGTH: 488
<212> TYPE: PRT
<213> ORGANISM: Simian T-cell lymphotropic virus type 1

<400> SEQUENCE: 8

Met Gly Lys Phe Leu Ala Thr Leu Ile Leu Phe Phe Gln Phe Cys Pro
1               5                   10                  15

Leu Ile Leu Gly Asp Tyr Ser Pro Ser Cys Cys Thr Leu Thr Ile Gly
            20                  25                  30

Val Ser Ser Tyr Leu Ser Lys Pro Cys Asn Pro Ala Gln Pro Val Cys
        35                  40                  45

Ser Trp Thr Leu Asp Leu Leu Ala Leu Ser Ala Asp Gln Ala Leu Gln
    50                  55                  60

Pro Pro Cys Pro Asn Leu Val Ser Tyr Ser Ser Tyr His Ala Thr Tyr
65                  70                  75                  80

Ser Leu Tyr Leu Phe Pro His Trp Ile Lys Lys Pro Asn Arg Asn Gly
                85                  90                  95

Gly Gly Tyr Tyr Ser Ala Ser Tyr Ser Asp Pro Cys Ser Leu Lys Cys
            100                 105                 110

Pro Tyr Leu Gly Cys Gln Ser Trp Thr Cys Pro Tyr Thr Gly Val Val
        115                 120                 125

Ser Ser Pro Tyr Trp Lys Phe Gln Gln Asp Val Asn Phe Thr Gln Glu
    130                 135                 140

Val Ser His Leu Asn Ile Asn Leu His Phe Ser Lys Cys Gly Phe Pro
145                 150                 155                 160

Phe Ser Leu Leu Ile Asp Ala Pro Gly Tyr Asp Pro Ile Trp Phe Leu
                165                 170                 175

Asn Thr Glu Pro Ser Gln Leu Pro Pro Thr Ala Pro Leu Leu Pro
            180                 185                 190

His Ser Asn Leu Asp His Ile Leu Glu Pro Ser Ile Pro Trp Lys Ser
        195                 200                 205

Lys Leu Leu Thr Leu Val Gln Leu Thr Leu Gln Ser Thr Asn Tyr Thr
    210                 215                 220

Cys Ile Val Cys Ile Asp Arg Ala Ser Leu Ser Thr Trp His Val Leu
225                 230                 235                 240

Tyr Ser Pro Asn Val Ser Val Pro Ser Ser Ser Thr Pro Leu Leu
                245                 250                 255

Tyr Pro Ser Leu Ala Leu Pro Ala Pro His Leu Thr Leu Pro Phe Asn
            260                 265                 270

Trp Thr His Cys Phe Asp Pro Gln Ile Gln Ala Ile Val Ser Ser Pro
```

```
                275                 280                 285
Cys His Asn Ser Leu Ile Leu Pro Pro Phe Ser Leu Ser Pro Val Pro
            290                 295                 300

Thr Leu Gly Ser Arg Ser Arg Arg Ala Val Pro Val Ala Val Trp Leu
305                 310                 315                 320

Val Ser Ala Leu Ala Met Gly Ala Gly Ala Gly Gly Ile Thr Gly
                325                 330                 335

Ser Met Ser Leu Ala Ser Gly Lys Ser Leu Leu His Glu Val Asp Lys
            340                 345                 350

Asp Ile Ser Gln Leu Thr Gln Ala Ile Val Lys Asn His Lys Asn Leu
            355                 360                 365

Leu Lys Ile Ala Gln Tyr Ala Ala Gln Asn Arg Arg Gly Leu Asp Leu
        370                 375                 380

Leu Phe Trp Glu Gln Gly Gly Leu Cys Lys Ala Leu Gln Glu Gln Cys
385                 390                 395                 400

Cys Phe Leu Asn Ile Thr Asn Ser His Val Ser Ile Leu Gln Glu Arg
                405                 410                 415

Pro Pro Leu Glu Asn Arg Val Leu Thr Gly Trp Gly Leu Asn Trp Asp
            420                 425                 430

Leu Gly Leu Ser Gln Trp Ala Arg Glu Ala Leu Gln Thr Gly Ile Thr
        435                 440                 445

Leu Val Ala Leu Leu Leu Val Ile Leu Ala Gly Pro Cys Ile Leu
        450                 455                 460

Arg Gln Leu Arg His Leu Pro Ser Arg Val Arg Tyr Pro His Tyr Ser
465                 470                 475                 480

Leu Ile Asn Pro Glu Ser Ser Leu
                485

<210> SEQ ID NO 9
<211> LENGTH: 1461
<212> TYPE: DNA
<213> ORGANISM: Simian T-cell lymphotropic virus type 2
<220> FEATURE:
<221> NAME/KEY: CDS
<222> LOCATION: (1)..(1461)

<400> SEQUENCE: 9 atg ggt aag ata att gct ttc ctt tta ttc cat ctt aca tgt atc aca    48
Met Gly Lys Ile Ile Ala Phe Leu Leu Phe His Leu Thr Cys Ile Thr
1               5                   10                  15 atc act aaa cag agc cgg tgc acg ctt acg gta ggt gtc tcc tcg tat    96
Ile Thr Lys Gln Ser Arg Cys Thr Leu Thr Val Gly Val Ser Ser Tyr
            20                  25                  30 cac tct agt ccc tgc agt ctt gcc caa cct atc tgc acc tgg gat ctc   144
His Ser Ser Pro Cys Ser Leu Ala Gln Pro Ile Cys Thr Trp Asp Leu
        35                  40                  45 gac ctt cat tcc tta act aca gac caa cgt ctg tac cct cca tgc ccc   192
Asp Leu His Ser Leu Thr Thr Asp Gln Arg Leu Tyr Pro Pro Cys Pro
    50                  55                  60 aat cta gtt tct tac tct aac ttc cac aag tcc tac tcc tta tat ttg   240
Asn Leu Val Ser Tyr Ser Asn Phe His Lys Ser Tyr Ser Leu Tyr Leu
65                  70                  75                  80 ttc ccg cac tgg gta aaa aag cca aat aga caa ggc ctg gga tac tat   288
Phe Pro His Trp Val Lys Lys Pro Asn Arg Gln Gly Leu Gly Tyr Tyr
                85                  90                  95 tct gca tcc tac agc gac ccc tgc tcg ctc cag tgc cct tat tta gga   336
Ser Ala Ser Tyr Ser Asp Pro Cys Ser Leu Gln Cys Pro Tyr Leu Gly
            100                 105                 110
```

-continued

```
agc cag tct tgg aca tgc cct tac acc ggc ccc atc tcc agc ccg tct    384
Ser Gln Ser Trp Thr Cys Pro Tyr Thr Gly Pro Ile Ser Ser Pro Ser
        115                 120                 125 tgg agg ttc cac cga gat gtt aac ttc acc caa gag gtc aac cat gta    432
Trp Arg Phe His Arg Asp Val Asn Phe Thr Gln Glu Val Asn His Val
130                 135                 140 acc ctc cgg cta cac ttc tcc cga tgt ggc tct tct atg acc ctc ctc    480
Thr Leu Arg Leu His Phe Ser Arg Cys Gly Ser Ser Met Thr Leu Leu
145                 150                 155                 160 ata gac gcc cca ggc tac gac ccc ctg tgg ttc atc tct tcg gaa ccc    528
Ile Asp Ala Pro Gly Tyr Asp Pro Leu Trp Phe Ile Ser Ser Glu Pro
                165                 170                 175 act cag ccc ccc ccc act tcc cca cca tta gtc cgc gac tct gac ctt    576
Thr Gln Pro Pro Pro Thr Ser Pro Pro Leu Val Arg Asp Ser Asp Leu
            180                 185                 190 gaa cat atc tta acc ccc tcc tcc tgg gct act agg atg cta acc        624
Glu His Ile Leu Thr Pro Ser Ser Ser Trp Ala Thr Arg Met Leu Thr
        195                 200                 205 ctc atc caa cta act cta caa agt acc aat tat tct tgc atg gtt tgt    672
Leu Ile Gln Leu Thr Leu Gln Ser Thr Asn Tyr Ser Cys Met Val Cys
    210                 215                 220 ata gac aga acc agc ttg tcg tcc tgg cac gta ctc tat acc cct aat    720
Ile Asp Arg Thr Ser Leu Ser Ser Trp His Val Leu Tyr Thr Pro Asn
225                 230                 235                 240 atc tct gcc tca cct ggg ggc gac tcc ttg cct ata ctt tat ccc tcc    768
Ile Ser Ala Ser Pro Gly Gly Asp Ser Leu Pro Ile Leu Tyr Pro Ser
                245                 250                 255 ttg gcc cta ccg gcc ccc caa ccc cag ccg ttt tcc tgg tct cac tgt    816
Leu Ala Leu Pro Ala Pro Gln Pro Gln Pro Phe Ser Trp Ser His Cys
            260                 265                 270 tac cag ccc cac cta cag gca gta act aca gcc aat tgc aac aat tcc    864
Tyr Gln Pro His Leu Gln Ala Val Thr Thr Ala Asn Cys Asn Asn Ser
        275                 280                 285 att gtc ctg ccc cca ttc tct ctc acc ccg gtg cct tcc cct ggg aca    912
Ile Val Leu Pro Pro Phe Ser Leu Thr Pro Val Pro Ser Pro Gly Thr
    290                 295                 300 aga agc cgc cgg gct att cca gtg gct gta tgg ctc gtc tca gcc cta    960
Arg Ser Arg Arg Ala Ile Pro Val Ala Val Trp Leu Val Ser Ala Leu
305                 310                 315                 320 gcg gcc ggg act ggt att gca ggg gga ata acc gga tcc ctg tcc cta   1008
Ala Ala Gly Thr Gly Ile Ala Gly Gly Ile Thr Gly Ser Leu Ser Leu
                325                 330                 335 gca tca agc cgc agc ctg ctt ttt gaa gtt gac aaa gat att tcc cac   1056
Ala Ser Ser Arg Ser Leu Leu Phe Glu Val Asp Lys Asp Ile Ser His
            340                 345                 350 ctc aca caa gcc atc gtt aaa aac cat caa aac atc ctc cgc gta gca   1104
Leu Thr Gln Ala Ile Val Lys Asn His Gln Asn Ile Leu Arg Val Ala
        355                 360                 365 caa tat gca gcc caa aat aga aga gga cta gac ctc ctg ttt tgg gaa   1152
Gln Tyr Ala Ala Gln Asn Arg Arg Gly Leu Asp Leu Leu Phe Trp Glu
    370                 375                 380 caa gga ggc ctc tgc aaa gcc ata caa gag caa tgt tgc ttc ctt aac   1200
Gln Gly Gly Leu Cys Lys Ala Ile Gln Glu Gln Cys Cys Phe Leu Asn
385                 390                 395                 400 atc agc aac acc cat gtg tcc gtc ctt cag gag cgc ccc ccc ctg gaa   1248
Ile Ser Asn Thr His Val Ser Val Leu Gln Glu Arg Pro Pro Leu Glu
                405                 410                 415 aag aga gtc atc aca gga tgg ggt ctc aac tgg gac cta ggg cta tcc   1296
Lys Arg Val Ile Thr Gly Trp Gly Leu Asn Trp Asp Leu Gly Leu Ser
```

```
                420                 425                 430
caa tgg gca cgg gaa gca ctc caa act ggt ata acc atc cta gcc ttg    1344
Gln Trp Ala Arg Glu Ala Leu Gln Thr Gly Ile Thr Ile Leu Ala Leu
        435                 440                 445 ctc ctc ctt gtc ata ctg ttc ggt cct tgt atc ctt cgc caa ctc caa    1392
Leu Leu Leu Val Ile Leu Phe Gly Pro Cys Ile Leu Arg Gln Leu Gln
450                 455                 460 tca ctt ccc cac cgg cta cag aac agg cac aac caa tac tct ctt att    1440
Ser Leu Pro His Arg Leu Gln Asn Arg His Asn Gln Tyr Ser Leu Ile
465                 470                 475                 480 aac cag gaa acc aca cta taa                                        1461
Asn Gln Glu Thr Thr Leu
                485

<210> SEQ ID NO 10
<211> LENGTH: 486
<212> TYPE: PRT
<213> ORGANISM: Simian T-cell lymphotropic virus type 2

<400> SEQUENCE: 10

Met Gly Lys Ile Ile Ala Phe Leu Leu Phe His Leu Thr Cys Ile Thr
1               5                   10                  15

Ile Thr Lys Gln Ser Arg Cys Thr Leu Thr Val Gly Val Ser Ser Tyr
            20                  25                  30

His Ser Ser Pro Cys Ser Leu Ala Gln Pro Ile Cys Thr Trp Asp Leu
        35                  40                  45

Asp Leu His Ser Leu Thr Thr Asp Gln Arg Leu Tyr Pro Pro Cys Pro
    50                  55                  60

Asn Leu Val Ser Tyr Ser Asn Phe His Lys Ser Tyr Ser Leu Tyr Leu
65                  70                  75                  80

Phe Pro His Trp Val Lys Lys Pro Asn Arg Gln Gly Leu Gly Tyr Tyr
                85                  90                  95

Ser Ala Ser Tyr Ser Asp Pro Cys Ser Leu Gln Cys Pro Tyr Leu Gly
            100                 105                 110

Ser Gln Ser Trp Thr Cys Pro Tyr Thr Gly Pro Ile Ser Ser Pro Ser
        115                 120                 125

Trp Arg Phe His Arg Asp Val Asn Phe Thr Gln Glu Val Asn His Val
    130                 135                 140

Thr Leu Arg Leu His Phe Ser Arg Cys Gly Ser Ser Met Thr Leu Leu
145                 150                 155                 160

Ile Asp Ala Pro Gly Tyr Asp Pro Leu Trp Phe Ile Ser Ser Glu Pro
                165                 170                 175

Thr Gln Pro Pro Pro Thr Ser Pro Pro Leu Val Arg Asp Ser Asp Leu
            180                 185                 190

Glu His Ile Leu Thr Pro Ser Ser Trp Ala Thr Arg Met Leu Thr
        195                 200                 205

Leu Ile Gln Leu Thr Leu Gln Ser Thr Asn Tyr Ser Cys Met Val Cys
    210                 215                 220

Ile Asp Arg Thr Ser Leu Ser Ser Trp His Val Leu Tyr Thr Pro Asn
225                 230                 235                 240

Ile Ser Ala Ser Pro Gly Gly Asp Ser Leu Pro Ile Tyr Pro Ser
                245                 250                 255

Leu Ala Leu Pro Ala Pro Gln Pro Gln Pro Phe Ser Trp Ser His Cys
            260                 265                 270

Tyr Gln Pro His Leu Gln Ala Val Thr Thr Ala Asn Cys Asn Asn Ser
        275                 280                 285
```

```
Ile Val Leu Pro Pro Phe Ser Leu Thr Pro Val Pro Ser Pro Gly Thr
    290                 295                 300

Arg Ser Arg Arg Ala Ile Pro Val Ala Val Trp Leu Val Ser Ala Leu
305                 310                 315                 320

Ala Ala Gly Thr Gly Ile Ala Gly Gly Ile Thr Gly Ser Leu Ser Leu
                325                 330                 335

Ala Ser Ser Arg Ser Leu Leu Phe Glu Val Asp Lys Asp Ile Ser His
                340                 345                 350

Leu Thr Gln Ala Ile Val Lys Asn His Gln Asn Ile Leu Arg Val Ala
            355                 360                 365

Gln Tyr Ala Ala Gln Asn Arg Arg Gly Leu Asp Leu Leu Phe Trp Glu
    370                 375                 380

Gln Gly Gly Leu Cys Lys Ala Ile Gln Glu Gln Cys Cys Phe Leu Asn
385                 390                 395                 400

Ile Ser Asn Thr His Val Ser Val Leu Gln Glu Arg Pro Pro Leu Glu
                405                 410                 415

Lys Arg Val Ile Thr Gly Trp Gly Leu Asn Trp Asp Leu Gly Leu Ser
                420                 425                 430

Gln Trp Ala Arg Glu Ala Leu Gln Thr Gly Ile Thr Ile Leu Ala Leu
            435                 440                 445

Leu Leu Leu Val Ile Leu Phe Gly Pro Cys Ile Leu Arg Gln Leu Gln
    450                 455                 460

Ser Leu Pro His Arg Leu Gln Asn Arg His Asn Gln Tyr Ser Leu Ile
465                 470                 475                 480

Asn Gln Glu Thr Thr Leu
                485

<210> SEQ ID NO 11
<211> LENGTH: 930
<212> TYPE: DNA
<213> ORGANISM: Simian T-cell lymphotropic virus type 3
<220> FEATURE:
<221> NAME/KEY: CDS
<222> LOCATION: (1)..(930)

<400> SEQUENCE: 11 atg ggt aag ttt ggc ctt tat tgt ctt gtt cac ctt tac ata ctt ctc      48
Met Gly Lys Phe Gly Leu Tyr Cys Leu Val His Leu Tyr Ile Leu Leu
1               5                   10                  15 cct gcc tcc tct ggc aat ccc agt cgg tgc acc ctg ttc ata ggg gcc      96
Pro Ala Ser Ser Gly Asn Pro Ser Arg Cys Thr Leu Phe Ile Gly Ala
                20                  25                  30 tct tcc tac cac tcc agc cct tgc ggg tcc agc ctc cca cgg tgt acc     144
Ser Ser Tyr His Ser Ser Pro Cys Gly Ser Ser Leu Pro Arg Cys Thr
            35                  40                  45 tgg aat ctt gac cta ttc tcc ctc acg aaa gat caa agc cta agc ccc     192
Trp Asn Leu Asp Leu Phe Ser Leu Thr Lys Asp Gln Ser Leu Ser Pro
        50                  55                  60 cca tgt cca gac tta att act tac tca caa tac cac aag ccc tac tcc     240
Pro Cys Pro Asp Leu Ile Thr Tyr Ser Gln Tyr His Lys Pro Tyr Ser
65                  70                  75                  80 ctg tat gta ttc cct cat tgg ata act aaa cct aac cgc cgg ggc tta     288
Leu Tyr Val Phe Pro His Trp Ile Thr Lys Pro Asn Arg Arg Gly Leu
                85                  90                  95 ggt tac tat tcc gct tcc tac tca gac ccc tgt gcc ata cag tgc cct     336
Gly Tyr Tyr Ser Ala Ser Tyr Ser Asp Pro Cys Ala Ile Gln Cys Pro
                100                 105                 110
```

```
tac ctg gga tgc cag tcg tgg aca tgc ccc tat acg ggc ccg gtg tcc   384
Tyr Leu Gly Cys Gln Ser Trp Thr Cys Pro Tyr Thr Gly Pro Val Ser
            115                 120                 125 agt ccg cat tgg aga tac acc tat gat ctt aac ttt acc cag gag gta   432
Ser Pro His Trp Arg Tyr Thr Tyr Asp Leu Asn Phe Thr Gln Glu Val
    130                 135                 140 tca tcc gtc tcc tta cac ttg cat ttc tcc aaa tgc gga tcc tcg ttc   480
Ser Ser Val Ser Leu His Leu His Phe Ser Lys Cys Gly Ser Ser Phe
145                 150                 155                 160 tcc ttt cta cta gac gca cca gga tat gac cca gtg tgg ttc ctc tcc   528
Ser Phe Leu Leu Asp Ala Pro Gly Tyr Asp Pro Val Trp Phe Leu Ser
                165                 170                 175 tcc cag gcc aca cag gct cca ccc aca cct gcc cct ctc ata cgg gac   576
Ser Gln Ala Thr Gln Ala Pro Pro Thr Pro Ala Pro Leu Ile Arg Asp
            180                 185                 190 tca gat ctc cag tac att cta gaa ccg ccc att ccg tgg agc tct aag   624
Ser Asp Leu Gln Tyr Ile Leu Glu Pro Pro Ile Pro Trp Ser Ser Lys
        195                 200                 205 att ctt aac ctt atc ctc ctc acc cta aaa agc act aac tat tct tgc   672
Ile Leu Asn Leu Ile Leu Leu Thr Leu Lys Ser Thr Asn Tyr Ser Cys
210                 215                 220 atg gtc tgt gtt gac cgc tcc agc cta tcc tca tgg cat gtc ctg tat   720
Met Val Cys Val Asp Arg Ser Ser Leu Ser Ser Trp His Val Leu Tyr
225                 230                 235                 240 gga ccc act caa gtc ccc agt cca ccc gac ccc caa gcc cgg tct atc   768
Gly Pro Thr Gln Val Pro Ser Pro Pro Asp Pro Gln Ala Arg Ser Ile
                245                 250                 255 ctg cga cct gcc tta gct att ccc gcc agt aat atc acc ccc ccg ttt   816
Leu Arg Pro Ala Leu Ala Ile Pro Ala Ser Asn Ile Thr Pro Pro Phe
            260                 265                 270 cct tgg acc cat tgc tat cgc cct cct ccg caa gcc atc tcc tcg gag   864
Pro Trp Thr His Cys Tyr Arg Pro Pro Pro Gln Ala Ile Ser Ser Glu
        275                 280                 285 aat tgt aac aac tct gta gtg ctg ccc ccc ttt tct ctg tct cca att   912
Asn Cys Asn Asn Ser Val Val Leu Pro Pro Phe Ser Leu Ser Pro Ile
    290                 295                 300 cct aac gtc tcc aga ccc                                           930
Pro Asn Val Ser Arg Pro
305                 310

<210> SEQ ID NO 12
<211> LENGTH: 310
<212> TYPE: PRT
<213> ORGANISM: Simian T-cell lymphotropic virus type 3

<400> SEQUENCE: 12

Met Gly Lys Phe Gly Leu Tyr Cys Leu Val His Leu Tyr Ile Leu Leu
 1               5                  10                  15

Pro Ala Ser Ser Gly Asn Pro Ser Arg Cys Thr Leu Phe Ile Gly Ala
             20                  25                  30

Ser Ser Tyr His Ser Ser Pro Cys Gly Ser Ser Leu Pro Arg Cys Thr
         35                  40                  45

Trp Asn Leu Asp Leu Phe Ser Leu Thr Lys Asp Gln Ser Leu Ser Pro
     50                  55                  60

Pro Cys Pro Asp Leu Ile Thr Tyr Ser Gln Tyr His Lys Pro Tyr Ser
 65                  70                  75                  80

Leu Tyr Val Phe Pro His Trp Ile Thr Lys Pro Asn Arg Arg Gly Leu
                 85                  90                  95

Gly Tyr Tyr Ser Ala Ser Tyr Ser Asp Pro Cys Ala Ile Gln Cys Pro
```

```
                100                 105                 110
Tyr Leu Gly Cys Gln Ser Trp Thr Cys Pro Tyr Thr Gly Pro Val Ser
            115                 120                 125
Ser Pro His Trp Arg Tyr Thr Tyr Asp Leu Asn Phe Thr Gln Glu Val
        130                 135                 140
Ser Ser Val Ser Leu His Leu His Phe Ser Lys Cys Gly Ser Ser Phe
145                 150                 155                 160
Ser Phe Leu Leu Asp Ala Pro Gly Tyr Asp Pro Val Trp Phe Leu Ser
                165                 170                 175
Ser Gln Ala Thr Gln Ala Pro Pro Thr Pro Ala Pro Leu Ile Arg Asp
            180                 185                 190
Ser Asp Leu Gln Tyr Ile Leu Glu Pro Pro Ile Pro Trp Ser Ser Lys
        195                 200                 205
Ile Leu Asn Leu Ile Leu Leu Thr Leu Lys Ser Thr Asn Tyr Ser Cys
        210                 215                 220
Met Val Cys Val Asp Arg Ser Ser Leu Ser Ser Trp His Val Leu Tyr
225                 230                 235                 240
Gly Pro Thr Gln Val Pro Ser Pro Asp Pro Gln Ala Arg Ser Ile
                245                 250                 255
Leu Arg Pro Ala Leu Ala Ile Pro Ala Ser Asn Ile Thr Pro Pro Phe
            260                 265                 270
Pro Trp Thr His Cys Tyr Arg Pro Pro Gln Ala Ile Ser Ser Glu
        275                 280                 285
Asn Cys Asn Asn Ser Val Val Leu Pro Pro Phe Ser Leu Ser Pro Ile
        290                 295                 300
Pro Asn Val Ser Arg Pro
305                 310

<210> SEQ ID NO 13
<211> LENGTH: 153
<212> TYPE: DNA
<213> ORGANISM: Human T-cell lymphotropic virus type 1
<220> FEATURE:
<221> NAME/KEY: CDS
<222> LOCATION: (1)..(153)

<400> SEQUENCE: 13 att aaa aag cca aac cca aat ggc gga ggc tat tat tta gcc tct tat    48
Ile Lys Lys Pro Asn Pro Asn Gly Gly Gly Tyr Tyr Leu Ala Ser Tyr
  1               5                  10                  15 tca gac cct tgt tcc tta aaa tgc cca tac ctg ggg tgc caa tca tgg    96
Ser Asp Pro Cys Ser Leu Lys Cys Pro Tyr Leu Gly Cys Gln Ser Trp
              20                  25                  30 acc tgc ccc tat aca gga gcc gtc tcc agc ccc tac tgg aag ttt cag   144
Thr Cys Pro Tyr Thr Gly Ala Val Ser Ser Pro Tyr Trp Lys Phe Gln
          35                  40                  45 caa gat gtc                                                        153
Gln Asp Val
    50

<210> SEQ ID NO 14
<211> LENGTH: 51
<212> TYPE: PRT
<213> ORGANISM: Human T-cell lymphotropic virus type 1

<400> SEQUENCE: 14

Ile Lys Lys Pro Asn Pro Asn Gly Gly Gly Tyr Tyr Leu Ala Ser Tyr
  1               5                  10                  15
```

```
Ser Asp Pro Cys Ser Leu Lys Cys Pro Tyr Leu Gly Cys Gln Ser Trp
            20                  25                  30

Thr Cys Pro Tyr Thr Gly Ala Val Ser Ser Pro Tyr Trp Lys Phe Gln
        35                  40                  45

Gln Asp Val
    50

<210> SEQ ID NO 15
<211> LENGTH: 153
<212> TYPE: DNA
<213> ORGANISM: Human T-cell lymphotropic virus type 1
<220> FEATURE:
<221> NAME/KEY: CDS
<222> LOCATION: (1)..(153)

<400> SEQUENCE: 15 gtt aaa aag cca aac cga aat ggc gga ggc tat tat tta gcc tct tat      48
Val Lys Lys Pro Asn Arg Asn Gly Gly Gly Tyr Tyr Leu Ala Ser Tyr
 1               5                  10                  15 tca gac cct tgt tcc tta aaa tgc cca tac ctg ggg tgc caa tca tgg      96
Ser Asp Pro Cys Ser Leu Lys Cys Pro Tyr Leu Gly Cys Gln Ser Trp
            20                  25                  30 acc tgc ccc tat aca gga gcc gtc tcc agc ccc tac tgg aag ttt cag     144
Thr Cys Pro Tyr Thr Gly Ala Val Ser Ser Pro Tyr Trp Lys Phe Gln
        35                  40                  45 caa gat gtc                                                         153
Gln Asp Val
    50

<210> SEQ ID NO 16
<211> LENGTH: 51
<212> TYPE: PRT
<213> ORGANISM: Human T-cell lymphotropic virus type 1

<400> SEQUENCE: 16

Val Lys Lys Pro Asn Arg Asn Gly Gly Gly Tyr Tyr Leu Ala Ser Tyr
 1               5                  10                  15

Ser Asp Pro Cys Ser Leu Lys Cys Pro Tyr Leu Gly Cys Gln Ser Trp
            20                  25                  30

Thr Cys Pro Tyr Thr Gly Ala Val Ser Ser Pro Tyr Trp Lys Phe Gln
        35                  40                  45

Gln Asp Val
    50

<210> SEQ ID NO 17
<211> LENGTH: 153
<212> TYPE: DNA
<213> ORGANISM: Human T-cell lymphotropic virus type 1
<220> FEATURE:
<221> NAME/KEY: CDS
<222> LOCATION: (1)..(153)

<400> SEQUENCE: 17 att aaa aag cca aac cga aat ggc gga ggc tat tat tta gcc tct tat      48
Ile Lys Lys Pro Asn Arg Asn Gly Gly Gly Tyr Tyr Leu Ala Ser Tyr
 1               5                  10                  15 tca gac cct tgt tcc tta aaa tgc cca tac ctg ggg tgc caa tca tgg      96
Ser Asp Pro Cys Ser Leu Lys Cys Pro Tyr Leu Gly Cys Gln Ser Trp
            20                  25                  30 acc tgc ccc tat aca gga gcc gtc tcc agc ccc tac tgg aag ttt caa     144
Thr Cys Pro Tyr Thr Gly Ala Val Ser Ser Pro Tyr Trp Lys Phe Gln
        35                  40                  45
```

```
caa gat gtc                                                         153
Gln Asp Val
    50

<210> SEQ ID NO 18
<211> LENGTH: 51
<212> TYPE: PRT
<213> ORGANISM: Human T-cell lymphotropic virus type 1

<400> SEQUENCE: 18

Ile Lys Lys Pro Asn Arg Asn Gly Gly Gly Tyr Tyr Leu Ala Ser Tyr
 1               5                  10                  15

Ser Asp Pro Cys Ser Leu Lys Cys Pro Tyr Leu Gly Cys Gln Ser Trp
            20                  25                  30

Thr Cys Pro Tyr Thr Gly Ala Val Ser Ser Pro Tyr Trp Lys Phe Gln
        35                  40                  45

Gln Asp Val
    50

<210> SEQ ID NO 19
<211> LENGTH: 153
<212> TYPE: DNA
<213> ORGANISM: Human T-cell lymphotropic virus type 1
<220> FEATURE:
<221> NAME/KEY: CDS
<222> LOCATION: (1)..(153)

<400> SEQUENCE: 19 att aaa aag cca aac cga aat ggc gga ggc tat tat tta gcc tct tat   48
Ile Lys Lys Pro Asn Arg Asn Gly Gly Gly Tyr Tyr Leu Ala Ser Tyr
 1               5                  10                  15 tca gac cct tgt tcc tta aaa tgc cca tac ctg ggg tgc caa tca tgg   96
Ser Asp Pro Cys Ser Leu Lys Cys Pro Tyr Leu Gly Cys Gln Ser Trp
            20                  25                  30 acc tgc ccc tat aca gga ccc gtc tcc agc ccc tac tgg aag ttt cag  144
Thr Cys Pro Tyr Thr Gly Pro Val Ser Ser Pro Tyr Trp Lys Phe Gln
        35                  40                  45 caa gat gtc                                                        153
Gln Asp Val
    50

<210> SEQ ID NO 20
<211> LENGTH: 51
<212> TYPE: PRT
<213> ORGANISM: Human T-cell lymphotropic virus type 1

<400> SEQUENCE: 20

Ile Lys Lys Pro Asn Arg Asn Gly Gly Gly Tyr Tyr Leu Ala Ser Tyr
 1               5                  10                  15

Ser Asp Pro Cys Ser Leu Lys Cys Pro Tyr Leu Gly Cys Gln Ser Trp
            20                  25                  30

Thr Cys Pro Tyr Thr Gly Pro Val Ser Ser Pro Tyr Trp Lys Phe Gln
        35                  40                  45

Gln Asp Val
    50

<210> SEQ ID NO 21
<211> LENGTH: 171
<212> TYPE: DNA
<213> ORGANISM: Human T-cell lymphotropic virus type 1
<220> FEATURE:
<221> NAME/KEY: CDS
<222> LOCATION: (1)..(171)
```

-continued

```
<400> SEQUENCE: 21 att aaa aag cca aac cga aat ggc gga ggc tat cat tca gcc tct tat      48
Ile Lys Lys Pro Asn Arg Asn Gly Gly Gly Tyr His Ser Ala Ser Tyr
 1               5                  10                  15 tca gac cct tgt tcc tta aag tgc cca tac ctg ggg tgc caa tca tgg      96
Ser Asp Pro Cys Ser Leu Lys Cys Pro Tyr Leu Gly Cys Gln Ser Trp
             20                  25                  30 acc tgc ccc tat gca gga gcc gtc tcc agc ccc tac tgg aag ttt cag     144
Thr Cys Pro Tyr Ala Gly Ala Val Ser Ser Pro Tyr Trp Lys Phe Gln
         35                  40                  45 caa gat gtc aat ttt acc cag gaa gta                                 171
Gln Asp Val Asn Phe Thr Gln Glu Val
     50                  55

<210> SEQ ID NO 22
<211> LENGTH: 57
<212> TYPE: PRT
<213> ORGANISM: Human T-cell lymphotropic virus type 1

<400> SEQUENCE: 22

Ile Lys Lys Pro Asn Arg Asn Gly Gly Gly Tyr His Ser Ala Ser Tyr
 1               5                  10                  15

Ser Asp Pro Cys Ser Leu Lys Cys Pro Tyr Leu Gly Cys Gln Ser Trp
             20                  25                  30

Thr Cys Pro Tyr Ala Gly Ala Val Ser Ser Pro Tyr Trp Lys Phe Gln
         35                  40                  45

Gln Asp Val Asn Phe Thr Gln Glu Val
     50                  55

<210> SEQ ID NO 23
<211> LENGTH: 153
<212> TYPE: DNA
<213> ORGANISM: Human T-cell lymphotropic virus type 2
<220> FEATURE:
<221> NAME/KEY: CDS
<222> LOCATION: (1)..(153)

<400> SEQUENCE: 23 ata aga aag cca aac aga cag ggc cta ggg tac tac tcg cct tcc tac      48
Ile Arg Lys Pro Asn Arg Gln Gly Leu Gly Tyr Tyr Ser Pro Ser Tyr
 1               5                  10                  15 aat gac cct tgc tcg cta caa tgc ccc tac ttg ggc tcc caa tca tgg      96
Asn Asp Pro Cys Ser Leu Gln Cys Pro Tyr Leu Gly Ser Gln Ser Trp
             20                  25                  30 aca tgc cca tac acg gcc ccc gtc tcc act cca tcc tgg aat ttt cat     144
Thr Cys Pro Tyr Thr Ala Pro Val Ser Thr Pro Ser Trp Asn Phe His
         35                  40                  45 tca gat gta                                                          153
Ser Asp Val
     50

<210> SEQ ID NO 24
<211> LENGTH: 51
<212> TYPE: PRT
<213> ORGANISM: Human T-cell lymphotropic virus type 2

<400> SEQUENCE: 24

Ile Arg Lys Pro Asn Arg Gln Gly Leu Gly Tyr Tyr Ser Pro Ser Tyr
 1               5                  10                  15

Asn Asp Pro Cys Ser Leu Gln Cys Pro Tyr Leu Gly Ser Gln Ser Trp
             20                  25                  30
```

```
Thr Cys Pro Tyr Thr Ala Pro Val Ser Thr Pro Ser Trp Asn Phe His
         35                  40                  45

Ser Asp Val
    50

<210> SEQ ID NO 25
<211> LENGTH: 11
<212> TYPE: PRT
<213> ORGANISM: Homo sapiens

<400> SEQUENCE: 25

Asn Ala Pro Gln Lys Val Ile Glu Glu Phe Tyr
1               5                   10

<210> SEQ ID NO 26
<211> LENGTH: 22
<212> TYPE: PRT
<213> ORGANISM: Homo sapiens

<400> SEQUENCE: 26

Asn Gln Thr Trp Val His Arg Tyr Gly Glu Ser Ile Leu Pro Thr Thr
1               5                   10                  15

Leu Thr Thr Leu Trp Ser
            20

<210> SEQ ID NO 27
<211> LENGTH: 10
<212> TYPE: PRT
<213> ORGANISM: Homo sapiens

<400> SEQUENCE: 27

Lys Ser Phe Glu Met Leu Ile Leu Gly Arg
1               5                   10

<210> SEQ ID NO 28
<211> LENGTH: 9
<212> TYPE: PRT
<213> ORGANISM: Homo sapiens

<400> SEQUENCE: 28

Asp Ser Ile Met Gly Asn Lys Asp Leu
1               5

<210> SEQ ID NO 29
<211> LENGTH: 14
<212> TYPE: PRT
<213> ORGANISM: Homo sapiens

<400> SEQUENCE: 29

Tyr Ser Thr Ser Ile Phe Glu Lys Ala Gly Val Gln Gln Pro
1               5                   10

<210> SEQ ID NO 30
<211> LENGTH: 10
<212> TYPE: PRT
<213> ORGANISM: Homo sapiens

<400> SEQUENCE: 30

Glu Gln Leu Pro Trp Met Ser Tyr Leu Ser
1               5                   10

<210> SEQ ID NO 31
<211> LENGTH: 7
```

```
<212> TYPE: PRT
<213> ORGANISM: Homo sapiens

<400> SEQUENCE: 31

Gln Tyr Val Glu Gln Leu Cys
 1               5

<210> SEQ ID NO 32
<211> LENGTH: 13
<212> TYPE: PRT
<213> ORGANISM: Homo sapiens

<400> SEQUENCE: 32

Ile Val Gly Met Cys Phe Gln Tyr Val Glu Gln Leu Cys
 1               5                  10
```

GLUT-1 AS A RECEPTOR FOR HTLV ENVELOPES AND ITS USES

This application is a division of application Ser. No. 10/555,289 filed on Nov. 2, 2005; which is the 35 U.S.C. 371 national stage of International application PCT/EP04/04624 filed on Apr. 30, 2004; which claimed priority to Europe application 03291067.1 filed May 2, 2003. The entire contents of each of the above-identified applications are hereby incorporated by reference.

FIELD OF THE INVENTION

The invention relates to the use of the ubiquitous vertebrate glucose transporter GLUT1 represented by SEQ ID NO: 2, or of fragments or sequences derived thereof, for the in vitro diagnosis of cancers, when used as a tumor marker, or for the screening of compounds useful for the preparation of drugs for the prevention or the treatment of pathologies linked to an infection of an individual with a PTLV, or pathologies linked to an overexpression of GLUT1 on cell surfaces, or the in vitro detection of GLUT1 on cell surfaces. The invention also relates to pharmaceutical compositions containing GLUT1, or fragments or sequences derived thereof, and their uses such as in the frame of the prevention or the treatment of pathologies linked to an infection of an individual with a PTLV.

BACKGROUND OF THE INVENTION

The human T-cell leukemia virus (HTLV) is associated with leukemia and neurological syndromes. The role of viral envelopes in HTLV physiopathology is unclear and the envelope receptor, found in all vertebrate cell lines, remains unidentified.

HTLV envelope glycoproteins induce syncytium formation in vitro but their physiopathological effects are unclear. All vertebrate cell lines express functional HTLV envelope receptors, including cells resistant to HTLV envelope-mediated syncytium formation. We found that expression of the HTLV receptor-binding domain decreased lactate production due to diminished glucose consumption whereas binding-defective envelope mutants did not alter glucose metabolism. Glucose starvation increased HTLV receptor expression, reminiscent of nutrient sensing responses. Accordingly, overexpression of GLUT-1, the ubiquitous vertebrate glucose transporter, specifically increased HTLV envelope binding and GLUT-1 colocalized with HTLV envelopes. Moreover, HTLV envelope binding was highest in human erythrocytes, where GLUT-1 is abundantly expressed and is the sole glucose transporter isoform. These results demonstrate that GLUT-1 is an HTLV envelope receptor, and that this ligand/receptor interaction likely participates in the immunological and neurological disorders associated with HTLV infection.

SUMMARY OF THE INVENTION

Thus, the invention relates to the use of the ubiquitous vertebrate glucose transporter GLUT1 represented by SEQ ID NO: 2, or of fragments or sequences derived thereof, said fragments or derived sequences being able to bind to the envelope proteins of the primate T-cell leukemia viruses (PTLV), or of cells expressing GLUT1, for:
the screening of compounds useful for:
the preparation of drugs for the prevention or the treatment of pathologies linked to an infection of an individual with a PTLV,
the preparation of drugs for the prevention or the treatment of pathologies linked to an overexpression of GLUT1 on cell surfaces,
the in vitro detection of GLUT1 on cell surfaces,
said compounds being selected for their ability to bind specifically to said GLUT1,
the detection, concentration, and/or purification of PTLV or variants thereof, or of PTLV envelope proteins, or fragments thereof,
the preparation of drugs for the prevention or the treatment of pathologies either linked to an infection of an individual or an animal with a PTLV, such as HTLV-1, HTLV-2, STLV-1, STLV-2, STLV-3, or their variants, or linked to the presence of PTLV SU-related sequences in such individuals or animals,
the in vitro diagnosis of cancers, when used as a tumor marker.

For illustration purpose, screened compounds mentioned above can be selected for their ability to bind specifically to said GLUT1, or fragments of GLUT1, according to the following method using a EGFP-tagged GLUT1-binding component derived from PTLV RBD (receptor binding domain) as an example of such compound able to bind to GLUT1.

A EGFP-tagged Glut1-binding component derived from PTLV RBD is applied onto live or fixed suspension or attached cells. After washes with appropriate buffer, cells are incubated for 30 min at RT, washed and analyzed or quantified as attached on an appropriate support on a fluorescent microscope or as individual cell suspension on a fluorescent analysis ell sorter (FACS). Alternatively, a non-fluorescent GLUT1-binding component derived from PTLV RBD is applied as described above and revealed with a secondary fluorochrome-tagged reagent such as a fluorochrome-tagged secondary antibody directed against the PTLV RBD or against a non fluorochrome tag attached to the said PTLV RBD component.

The invention relates more particularly to the use as defined above, of fragments of GLUT1 chosen among the followings:

| | |
|---|---|
| SEQ ID NO: 25: | NAPQKVIEEFY |
| SEQ ID NO: 26: | NQTWVHRYGESILPTTLTTLWS |
| SEQ ID NO: 27: | KSFEMLILGR |
| SEQ ID NO: 28: | DSIMGNKDL |
| SEQ ID NO: 29: | YSTSIFEKAGVQQP |
| SEQ ID NO: 30: | EQLPWMSYLS |
| SEQ ID NO: 31: | QYVEQLC |
| SEQ ID NO: 32: | IVGMCFQYVEQLC |

These fragments of GLUT1 correspond to the predicted extracellular loops of human GLUT1 as described by Mueckler, M., and C. Makepeace. 1997. Identification of an amino acid residue that lies between the exofacial vestibule and exofacial substrate-binding site of the GLUT1 sugar permeation pathway. J Biol Chem. 272(48):30141-6.

The invention also concerns the use of compounds selected for their ability to bind specifically to GLUT1 as defined above, for the preparation of drugs for the prevention or the treatment of pathologies linked to an infection of an individual with a PTLV, such as pathologies corresponding to adult T cell leukemia (ATL), HTLV-I-associated myelopathy/tropical spastic paraparesis (HAM/TSP), as well as other HTLV-associated syndromes such as large granular lymphocyte (LGL) leukaemia (Loughran, T. P., K. G. Hadlock, R. Perzova, T. C. Gentile, Q. Yang, S. K. Foung, and B. J. Poiesz. 1998. Epitope mapping of HTLV envelope seroreactivity in LGL leukaemia. Br J. Haematol. 101(2):318-24), uveitis (Mochizuki, M., A. Ono, E. Ikeda, N. Hikita, T. Watanabe, K. Yamaguchi, K. Sagawa, and K. Ito. 1996. HTLV-I uveitis. J Acquir Immune Defic Syndr Hum Retrovirol. 13 Suppl 1:S50-6), infective dermatitis (La Grenade, L., R. A. Schwartz, and C. K. Janniger. 1996. Childhood dermatitis in the tropics: with special emphasis on infective dermatitis, a marker for infection with human T-cell leukemia virus-I. Cutis. 58(2):115-8), arthropathies (Nishioka, K., T. Sumida, and T. Hasunuma. 1996. Human T lymphotropic virus type I in arthropathy and autoimmune disorders. Arthritis Rheum. 39(8):1410-8), cutaneous T cell lymphoma (mycosis fungoides) (1. Hall, W. W., C. R. Liu, O. Schneewind, H. Takahashi, M. H. Kaplan, G. Roupe, and A. Vahlne. 1991. Deleted HTLV-I provirus in blood and cutaneous lesions of patients with mycosis fungoides. Science. 253(5017):317-20. 2. Zucker-Franklin, D., B. A. Pancake, M. Marmor, and P. M. Legler. 1997. Reexamination of human T cell lymphotropic virus (HTLV-I/II) prevalence. Proc Natl Acad Sci USA. 94(12):6403-7), polymyositis (Saito M, Higuchi I, Saito A, Izumo S, Usuku K, Bangham C R, Osame M. Molecular analysis of T cell clonotypes in muscle-infiltrating lymphocytes from patients with human T lymphotropic virus type 1 polymyositis. J Infect Dis. 2002 Nov. 1; 186(9):1231-41), and potentially other idiopathic diseases in which PTLV or PTLV sequences may be involved.

The invention relates more particularly to the use for the preparation of drugs for the prevention or the treatment of pathologies linked to an infection of an individual with a PTLV, of compounds chosen among the followings:

androgenic steroids (36: May J M, Danzo B J. Photolabeling of the human erythrocyte glucose carrier with androgenic steroids. Biochim Biophys Acta. 1988 Aug. 18; 943(2):199-210), cytochalasin B, forskolin, dipyridamole, isobutylmethylxanthine (20: Hellwig B, Joost H G. Differentiation of erythrocyte-(GLUT1), liver-(GLUT2), and adipocyte-type (GLUT4) glucose transporters by binding of the inhibitory ligands cytochalasin B, forskolin, dipyridamole, and isobutylmethylxanthine. Mol Pharmacol. 1991 September; 40(3):383-9), ethanol (Krauss S W, Diamond I, Gordon A S. Selective inhibition by ethanol of the type 1 facilitative glucose transporter (GLUT1). Mol Pharmacol. 1994 June; 45(6):1281-6), genistein (Vera J C, Reyes A M, Carcamo J G, Velasquez F V, Rivas C I, Zhang R H, Strobel P, Iribarren R, Scher H I, Slebe J C, et al. Genistein is a natural inhibitor of hexose and dehydroascorbic acid transport through the glucose transporter, GLUT1. J Biol Chem. 1996 Apr. 12; 271(15):8719-24), cadmium (Lachaal M, Liu H, Kim S, Spangler R A, Jung C Y. Cadmium increases GLUT1 substrate binding affinity in vitro while reducing its cytochalasin B binding affinity. Biochemistry. 1996 Nov. 26; 35 (47):14958-62), barbiturate (el-Barbary A, Fenstermacher J D, Haspel H C. Barbiturate inhibition of GLUT-1 mediated hexose transport in human erythrocytes exhibits substrate dependence for equilibrium exchange but not unidirectional sugar flux. Biochemistry. 1996 Dec. 3; 35(48):15222-7), dehydroascorbic acid (Rumsey S C, Kwon O, Xu G W, Burant C F, Simpson I, Levine M. Glucose transporter isoforms GLUT1 and GLUT3 transport dehydroascorbic acid. J Biol. Chem. 1997 Jul. 25; 272(30):18982-9), tricyclic antidepressants (Pinkofsky H B, Dwyer D S, Bradley R J. The inhibition of GLUT1 glucose transport and cytochalasin B binding activity by tricyclic antidepressants. Life Sci. 2000; 66(3):271-8), oestradiol, genistein and the anti-oestrogens, faslodex (ICI 182780), tamoxifen (Afzal I, Cunningham P, Naftalin R J. Interactions of ATP, oestradiol, genistein and the anti-oestrogens, faslodex (ICI 182780) and tamoxifen, with the human erythrocyte glucose transporter, GLUT1. Biochem J. 2002 Aug. 1; 365(Pt 3):707-19), gamma agonists of peroxisome proliferator-activated receptors (PPAR) such as thiazolidinedione (troglitazone, pioglitazone, rosiglitazone) ("TZDs modify astrocyte metabolism and mitochondrial function, which could be beneficial in neurological conditions where glucose availability is reduced" from Dello Russo C, Gavrilyuk V, Weinberg G, Almeida A, Bolanos J P, Palmer J, Pelligrino D, Galea E, Feinstein D L. Peroxisome proliferator-activated receptor gamma thiazolidinedione agonists increase glucose metabolism in astrocytes. J Biol Chem. 2003 Feb. 21; 278(8):5828-36).

The invention also relates to the use of compounds selected for their ability to bind specifically to GLUT1 as defined above, for the preparation of drugs for the prevention or the treatment of pathologies linked to an overexpression of GLUT1 on cell surfaces, such as cancers, such as:

squamous cell carcinoma (Kunkel M, Reichert T E, Benz P, Lehr H A, Jeong J H, Wieand S, Bartenstein P, Wagner W, Whiteside T L. Cancer. 2003 Feb. 15; 97(4):1015-24), hypopharyngeal carcinoma (Mineta H, Miura K, Takebayashi S, Misawa K, Araki K, Misawa Y, Ueda Y. Anticancer Res. 2002 November-December; 22(6B):3489-94), breast cancer (Brown R S, Wahl R L. Overexpression of Glut-1 glucose transporter in human breast cancer. An immunohistochemical study. Cancer. 1993 Nov. 15; 72(10):2979-85), cervical carinoma (Mendez L E, Manci N, Cantuaria G, Gomez-Marin O, Penalver M, Braunschweiger P, Nadji M. Expression of glucose transporter-1 in cervical cancer and its precursors. Gynecol Oncol. 2002 August; 86(2):138-43), ovarian carcinoma (Cantuaria G, Fagotti A, Ferrandina G, Magalhaes A, Nadji M, Angioli R, Penalver M, Mancuso S, Scambia G.GLUT-1 expression in ovarian carcinoma: association with survival and response to chemotherapy. Cancer. 2001 Sep. 1; 92(5):1144-50), lung cancer (Ito T, Noguchi Y, Satoh S, Hayashi H, Inayama Y, Kitamura H. Expression of facilitative glucose transporter isoforms in lung carcinomas: its relation to histologic type, differentiation grade, and tumor stage. Mod Pathol. 1998 May; 11(5):437-43. Younes M, Brown R W, Stephenson M, Gondo M, Cagle P T. Overexpression of Glut1 and Glut3 in stage I nonsmall cell lung carcinoma is associated with poor survival. Cancer. 1997 Sep. 15; 80(6):1046-51), pancreatic cancer (Reske S N, Grillenberger K G, Glatting G, Port M, Hildebrandt M, Gansauge F, Beger H G. Overexpression of glucose transporter 1 and increased FDG uptake in pancreatic carcinoma. J Nucl Med. 1997 September; 38(9):1344-8), insulinoma (1: Boden G, Murer E, Mozzoli M. Glucose transporter proteins in human insulinoma. Ann Intern Med. 1994 Jul. 15; 121(2):109-12, inflammatory conditions, immune or auto-immune diseases, such as
  autoimmune myocarditis (Tokita N, Hasegawa S, Tsujimura E, Yutani K, Izumi T, Nishimura T. Serial changes in 14C-deoxyglucose and 201Tl uptake in autoimmune myocarditis in rats. J Nucl Med. 2001 February; 42(2):285-91),
  in the frame of CD28 T-cell activation (Frauwirth K A, Riley J L, Harris M H, Parry R V, Rathmell J C, Plas D R, Elstrom R L, June C H, Thompson C B. The CD28 signaling pathway regulates glucose metabolism. Immunity. 2002 June; 16(6):769-77),
  in the frame of immunomodulation (Moriguchi S, Kato M, Sakai K, Yamamoto S, Shimizu E. Decreased mitogen response of splenic lymphocytes in obese Zucker rats is associated with the decreased expression of glucose transporter 1 (GLUT-1). Am J Clin Nutr. 1998 June; 67(6):1124-9),
  disorders of the central nervous system, such as facilitated glucose transporter protein type 1 (GLUT1) deficiency syndrome (review in Klepper J, Voit T. Eur J Pediatr. 2002 June; 161(6):295-304.)

The invention relates more particularly to the use for the preparation of drugs for the prevention or the treatment of pathologies linked to an overexpression of GLUT1 on cell surfaces, of compounds chosen among the followings:
  polypeptides compounds corresponding to the envelope proteins of PTLV, or fragments or sequences derived thereof, said fragments or derived sequences being able to bind to GLUT1,
  glucose or derivatives such as galactose, 2-fluorodeoxyglucose, 2-deoxyglucose, 3-O-methylglucose
  androgenic steroids, cytochalasin B, forskolin, dipyridamole, isobutylmethylxanthine, ethanol, genistein, cadmium, barbiturate, dehydroascorbic acid, tricyclic antidepressants, oestradiol, anti-oestrogens, faslodex (ICI 182780), tamoxifen, gamma agonists of peroxisome proliferator-activated receptors (PPAR) such as thiazolidinedione, troglitazone, pioglitazone, rosiglitazone, as mentioned above.

The invention relates more particularly to the use of polypeptides corresponding to the envelope proteins of PTLV, or fragments or sequences derived thereof, said polypeptides being selected for their ability to bind specifically to the ubiquitous vertebrate glucose transporter GLUT1 represented by SEQ ID NO: 2, or of nucleotide sequences encoding said polypeptides, for the preparation of drugs for the prevention or the treatment of pathologies linked to an overexpression of GLUT1 on cell surfaces, and the in vitro diagnosis of said pathologies.

The invention concerns more particularly the use as defined above, of polypeptides able to bind to at least one of the above mentioned fragments of GLUT1 corresponding to SEQ ID NO: 25, SEQ ID NO: 26, SEQ ID NO: 27, SEQ ID NO: 28, SEQ ID NO: 29, SEQ ID NO: 30, SEQ ID NO: 31, and SEQ ID NO: 32.

The invention concerns more particularly the use as defined above, of polypeptides able to bind to at least the fragment of GLUT1 corresponding to SEQ ID NO: 32.

The invention concerns more particularly the use as defined above, of GLUT1 binding polypeptides mentioned above chosen among the followings:
  the envelope protein of HTLV-1 corresponding to SEQ ID NO: 4, or of HTLV-2 corresponding to SEQ ID NO: 6, or of STLV-1 corresponding to SEQ ID NO: 8, or of STLV-2 corresponding to SEQ ID NO: 10, or of STLV-3 corresponding to SEQ ID NO: 12,
  fragments of the envelope proteins of PTLV, said fragments corresponding to polypeptides delimited in their N-terminal extremity by the amino acid located in position 1 to 90, or in position 75 to 90, and in their C-terminal extremity by the amino acid located in position 135 to 245, or in position 135 to 150, of said envelope proteins of PTLV, such as SEQ ID NO: 4, 6, 8, 10, 12,
  fragments of the envelope proteins of PTLV, said fragments corresponding to the following polypeptides:
    the polypeptide delimited in its N-terminal extremity by the amino acid located in position 83 to 89, and in its C-terminal extremity by the amino acid located in position 139 to 145, of the envelope protein of the strain MT-2 of HTLV-1 corresponding to SEQ ID NO: 4,
    the polypeptide delimited in its N-terminal extremity by the amino acid located in position 79 to 85, and in its C-terminal extremity by the amino acid located in position 135 to 141, of the envelope protein of the strain NRA of HTLV-2 corresponding to SEQ ID NO: 6,
    the polypeptide delimited in its N-terminal extremity by the amino acid located in position 83 to 89, and in its C-terminal extremity by the amino acid located in position 139 to 145, of the envelope protein of STLV-1 corresponding to SEQ ID NO: 8,
    the polypeptide delimited in its N-terminal extremity by the amino acid located in position 79 to 85, and in its C-terminal extremity by the amino acid located in position 135 to 141, of the envelope protein of STLV-2 corresponding to SEQ ID NO: 10,
    the polypeptide delimited in its N-terminal extremity by the amino acid located in position 82 to 88, and in its C-terminal extremity by the amino acid located in position 138 to 144, of the envelope protein of STLV-3 corresponding to SEQ ID NO: 12,
    the polypeptide corresponding to the envelope protein of a variant of HTLV-1, said polypeptide having the following sequence SEQ ID NO: 14,

```
I K K P N P N G G G Y Y L A S Y S D
P C S L K C P Y L G C Q S W T C P Y
T G A V S S P Y W K F Q Q D V
``` the polypeptide corresponding to the envelope protein of a variant of HTLV-1, said polypeptide having the following sequence SEQ ID NO: 16,

```
V K K P N R N G G G Y Y L A S Y S D
P C S L K C P Y L G C Q S W T C P Y
T G A V S S P Y W K F Q Q D V
``` the polypeptide corresponding to the envelope protein of a variant of HTLV-1, said polypeptide having the following sequence SEQ ID NO: 18,

```
I K K P N R N G G G Y Y L A S Y S D
P C S L K C P Y L G C Q S W T C P Y
T G A V S S P Y W K F Q Q D V
``` the polypeptide corresponding to the envelope protein of a variant of HTLV-1, said polypeptide having the following sequence SEQ ID NO: 20,

```
I K K P N R N G G G Y Y L A S Y S D
P C S L K C P Y L G C Q S W T C P Y
T G P V S S P Y W K F Q Q D V
``` the polypeptide corresponding to the envelope protein of a variant of HTLV-1, said polypeptide having the following sequence SEQ ID NO: 22,

```
I K K P N R N G G G Y H S A S Y S D P
C S L K C P Y L G C Q S W T C P Y A G
A V S S P Y W K F Q Q D V N F T Q E V
``` the polypeptide corresponding to the envelope protein of a variant of HTLV-2, said polypeptide having the following sequence SEQ ID NO: 24,

```
I R K P N R Q G L G Y Y S P S Y N D
P C S L Q C P Y L G S Q S W T C P Y
T A P V S T P S W N F H S D V
```

The invention concerns more particularly the use mentioned above of GLUT1 binding polypeptides as defined above, characterized in that the treated or detected pathologies are the followings:
- solid tumors, such as brain tumors, squamous cell carcinoma, hypopharyngeal carcinoma, breast cancer, cervical carcinoma, ovarian carcinoma, pancreatic cancer, insulinoma,
- inflammatory conditions, such as multiple sclerosis, rhumatoid arthritis,
- immune or auto-immune diseases, such as autoimmune myocarditis, or in the frame of CD28 T-cell activation, or in the frame of immunomodulation, or systemic lupus erythematous,
- disorders of the central nervous system, such as facilitated glucose transporter protein type 1 (GLUT1) deficiency syndrome.

The invention relates more particularly to the use of compounds selected for their ability to bind specifically to GLUT1 as mentioned above, and more particularly GLUT1 binding polypeptides as defined above, for the in vitro detection of GLUT1 on cell surfaces in the frame of processes for the in vitro diagnosis of pathologies linked to an overexpression of GLUT1 on cell surfaces, such as pathologies defined above, said processes comprising the following steps:
- contacting a biological sample (such as tumor biopsies or cells or tissue manifesting or with a suspected aberrant GLUT1 expression profile) from an individual with a compound, and more particularly a GLUT1 binding polypeptide, as defined above, said compound, or GLUT1 binding polypeptide, being optionally labeled, or susceptible to be recognized by a labeled molecule,
- determining the level of said compound, or GLUT1 binding polypeptide, bound to the cells contained in the biological sample and comparison with the level of binding of said compound, or GLUT1 binding polypeptide, to cells contained in the biological sample from an healthy individual.

The invention concerns more particularly the use of compounds as defined above for the in vitro diagnosis of cancers, characterized in that the compounds used are chosen among the compounds defined above selected for their ability to bind specifically to GLUT1.

The invention relates more particularly to the use as defined above, of GLUT1 binding polypeptides, or of nucleotide sequences encoding said polypeptides, for the preparation of drug vectors containing at their surface said polypeptides, said vectors being useful for targeting GLUT1 overexpressing cells for the prevention or the treatment of pathologies linked to an overexpression of GLUT1 on cell surfaces, said vectors containing molecules active against said pathologies, or containing genes in the frame of gene therapy of these pathologies.

The invention relates more particularly to the use as defined above, of GLUT1 binding polypeptides, or of nucleotide sequences encoding said polypeptides, for the preparation of drug vectors containing at their surface GLUT1 binding polypeptides, said vectors being useful for targeting GLUT1 overexpressing tumor cells, or cells involved in the inflammatory mechanism, or activated cells of the immune system, or cells of the central nervous system, for the prevention or the treatment of related pathologies as defined above.

The invention concerns more particularly the use of GLUT1 binding polypeptides, or of nucleotide sequences encoding said polypeptides, for the preparation of drug vectors as defined above, wherein the molecules active against the pathologies are antitumor molecules, or molecules against inflammatory conditions, immune or auto-immune diseases, or disorders of the central nervous system.

The invention also relates to the use of nucleotide sequences encoding polypeptides compounds selected for their ability to bind specifically to GLUT1 as defined above, such as nucleotide sequences encoding the polypeptides defined above, or fragments thereof, for the preparation, by substitution of one or several nucleotides of said nucleotide sequences, of mutant nucleotide sequences encoding corresponding mutant polypeptides unable to bind to GLUT1.

The invention also concerns the use of mutant polypeptides unable to bind to GLUT1 as defined above:
- as a negative control in the frame of the screening of compounds able to bind specifically to the non mutated corresponding polypeptides, and thus liable to be used in the frame of the preparation of drugs for the prevention or the treatment of pathologies linked to an infection of an individual with a PTLV,
- for the preparation of drugs for the prevention or the treatment of pathologies linked to an infection of an individual with a PTLV.

The invention relates more particularly to the use as defined above, of mutant polypeptides corresponding to the polypeptides defined above, wherein:
- D in position 106 and/or Y in position 114 of the envelope protein of HTLV-1 corresponding to SEQ ID NO: 4,
- D in position 102 and/or Y in position 110 or of HTLV-2 corresponding to SEQ ID NO: 6,
- D in position 106 and/or Y in position 114 or of STLV-1 corresponding to SEQ ID NO: 8,
- D in position 102 and/or Y in position 110 or of STLV-2 corresponding to SEQ ID NO: 10,
- D in position 105 and/or Y in position 113 or of STLV-3 corresponding to SEQ ID NO: 12,
- D in position 18 and/or Y in position 26 of the polypeptides corresponding to SEQ ID NO: 14, 16, 18, 20, 22, and 24, are substituted by another aminoacid, natural or not, such as mutant polypeptides corresponding to the polypeptides mentioned above wherein said D and/or A residues are substituted by A.

The invention also relates to the use of mutant nucleotide sequences encoding corresponding mutant polypeptides unable to bind to GLUT1 as defined above, for the preparation of transgenic mammal cells expressing said mutant polypeptides, said cells having a negative transdominant effect with regard to PTLV, thus preventing infection and dissemination of this latter in the organism.

The invention also concerns pharmaceutical compositions containing GLUT1 represented by SEQ ID NO: 2, or fragments or sequences derived thereof, said fragments or derived sequences being able to bind to the envelope proteins of the primate T-cell leukemia viruses (PTLV), in association with a pharmaceutically acceptable carrier.

The invention relates more particularly to pharmaceutical compositions containing mutant polypeptides corresponding to the polypeptides defined above, wherein:

D in position 106 and/or Y in position 114 of the envelope protein of HTLV-1 corresponding to SEQ ID NO: 4, D in position 102 and/or Y in position 110 or of HTLV-2 corresponding to SEQ ID NO: 6, D in position 105 and/or Y in position 113 or of STLV-3 corresponding to SEQ ID NO: 12, D in position 18 and/or Y in position 26, of the polypeptides corresponding to SEQ ID NO: 14, 16, 18, 20, 22, and 24, are substituted by another aminoacid, natural or not, such as mutant polypeptides corresponding to the polypeptides mentioned above wherein said D and/or A residues are substituted by A, in association with a pharmaceutically acceptable carrier.

The invention also concerns transgenic mammal cells expressing mutant polypeptides unable to bind to GLUT1 as defined above, said cells having a negative transdominant effect with regard to PTLV, thus preventing infection and dissemination of this latter in the organism.

The invention relates more particularly to pharmaceutical compositions containing transgenic mammal cells as defined above, in association with a pharmaceutically acceptable carrier.

The invention also concerns therapeutic vectors useful for targeting GLUT1 overexpressing cells in pathologies linked to an overexpression of GLUT1 on cell surfaces, such as defined above, said vectors containing at their surface GLUT1 binding polypeptides chosen among those defined above, and containing molecules active against said pathologies, as defined above, or containing genes in the frame of gene therapy.

The invention relates more particularly to pharmaceutical compositions containing therapeutic vectors as described above, in association with a pharmaceutically acceptable carrier.

The invention also relates to a method for the screening of compounds useful for:

the preparation of drugs for the prevention or the treatment of pathologies linked to an infection of an individual with a PTLV, the preparation of drugs for the prevention or the treatment of pathologies linked to an overexpression of GLUT1 on cell surfaces, the in vitro detection of GLUT1 on cell surfaces, said method comprising:

the contacting of GLUT1 represented by SEQ ID NO: 2, or of fragments or sequences derived thereof, said fragments or derived sequences being able to bind to the envelope proteins of the primate T-cell leukemia viruses (PTLV), or of cells expressing GLUT1, with compounds to be tested, the selection of compounds able to bind specifically to GLUT1, or fragments or sequences derived thereof, as for example according to the method mentioned above.

The invention relates more particularly to a method for the screening of compounds useful for the prevention or the treatment of pathologies linked to an overexpression of GLUT1 on cell surfaces, and the in vitro diagnosis of said pathologies, comprising the steps described above:

The invention also concerns a method for the in vitro diagnosis pathologies linked to an overexpression of GLUT1 on cell surfaces, characterized in that it comprises:

contacting a biological sample (such as biopsies or cells or tissue manifesting or with a suspected aberrant GLUT1 expression profile) from an individual with compounds, and more particularly polypeptides, selected for their ability to bind specifically to GLUT1 as defined above, said compounds or polypeptides being optionally labeled, or susceptible to be recognized by a labeled molecule, determining the level of said compounds or polypeptides bound to the cells contained in the biological sample and comparison with the level of binding of said compound to cells contained in the biological sample from an healthy individual.

The invention relates more particularly to a method as defined above for the in vitro diagnosis of pathologies mentioned above.

The invention also concerns a kit for the in vitro diagnosis of pathologies linked to an overexpression of GLUT1 on cell surfaces as described above, comprising compounds, and more particularly polypeptides, selected for their ability to bind specifically to GLUT1 as defined above, said compounds or polypeptides being optionally labeled, and, if necessary reagents for the detection of the binding of said compounds or polypeptides to GLUT1 initially present on cell surfaces in the biological sample.

FIG. 3C illustrates the measurement of extracellular lactate in the medium of 293T cells one day post transfection with an irrelevant DNA (control), $H_{1RBD}$ or the $H1_{RBD}$ D106A and Y114A mutants. Data are representative of three independent experiments.

FIG. 4A illustrates the binding of $H1_{RBD}$, $H2_{RBD}$, $H2_{RBD}$ D102A mutant, and $A_{RB}D$ to control 293T cells or 293T cells overexpressing either GLUT-1 or PiT2.

FIG. 4B illustrates the binding of $H2_{RBD}$-EGFP to cells overexpressing GLUT-1-HA or GLUT-3-HA, and corresponding immunoblots using an anti-HA antibody.

FIG. 4C is immunoprecipitation analysis using anti-rabbit-Fc beads and probed with an anti-HA antibody. Total cell extracts were blotted using an anti-rabbit Fc or an anti-HA antibody.

FIG. 5 illustrates the infections titer of MLV particle pseudotypes with HTLV-2 or A-MLV envelopes on 293T cells following transfection of with irrelevant or interfering $H2_{RBD}$ expression vectors alone or in addition with GLUT-1, GLUT-3 or PiT-2 expression vectors.

DETAILED DESCRIPTION OF THE INVENTION

The invention is further illustrated with the detailed description hereafter of the determination of GLUT1 as a specific receptor for PTLV RBD.

The human T-cell leukemia virus (HTLV) type 1 and 2 are present in all areas of the world as endemic or sporadic infectious agents [Slattery, 1999]. The etiological role of HTLV-1 in adult T cell leukemia (ATL) and tropical spastic paraparesis/HTLV-associated myelopathy (TSP/HAM) has been well established [Poiesz, 1980; Yoshida, 1982; Gessain, 1985; Osame, 1986]. The apparently restricted tropism of HTLV to T lymphocytes in infected patients[Cavrois, 1996; Hanon, 2000] contrasts with the ability of the viral-encoded envelope glycoprotein (Env) to bind to and direct entry into all vertebrate cell types tested in vitro[Sutton, 1996; Trejo, 2000; Kim, 2003]. Retroviral infections depend on early interactions between Env and cellular receptors. Identification of cellular receptors and coreceptors for other retroviral envelopes have helped to elucidate certain aspects of retrovirus physiopathology as well as their transmission and spreading within organisms and populations[Berger, 1999; Clapham, 2001; Weiss, 2002]. However, no clear association between HTLV Env and HTLV-associated diseases has been established and the identity of the receptor(s) for HTLV-1 and HTLV-2 Env has remained elusive.

Numerous cell surface components have been shown to play a role in HTLV Env-mediated syncytia formation [Niyogi, 2001; Daenke, 1999; Hildreth, 1997]. Nevertheless, HTLV Env-dependent cell membrane fusion and syncytia formation appear to be distinct from receptor binding per se [Denesvre, 1996; Daenke, 2000; Kim, 2000; Kim, 2003]. The search for HTLV Env receptor has been hindered in part by its ubiquitous presence [Sutton, 1996; Trejo, 2000; Jassal, 2001; Kim, 2003]. Additionally, the induction of rampant syncytium formation in cell culture upon expression of HTLV Env [Hoshino, 1983; Nagy, 1983] has prevented efficient and persistent Env expression. Based on our observation that the HTLV Env amino terminal domain shares striking structural and functional homology with that of murine leukemia viruses (MLV), we defined HTLV Env receptor-binding domain (RBD) and derived HTLV Env-based tools that overcome the problem of syncytia formation [Kim, 2000; Kim, 2003]. We were thus able to follow specific interactions between the Env RBD and a primary HTLV receptor. Using these tools, we have previously shown that the HTLV receptor is expressed on the surface on T lymphocytes, the major HTLV reservoir in vivo, only following T cell receptor activation[Manel, 2003].

Here we describe striking metabolic alterations in cell cultures following expression of HTLV envelopes as well as HTLV receptor binding domains. These alterations are characterized by a defect in the acidification of the cell culture medium associated with a decreased lactate production and a decline in glucose consumption and uptake. These observations as well as the knowledge that Env receptors for the related MLV and most of the gammaretrovirus belong to the family of multiple-membrane spanning transporters[Overbaugh, 2001] prompted us to test ubiquitous lactate and glucose transport-associated molecules as receptors for HTLV Env. We show that the ubiquitous GLUT-1 glucose transporter, present in all vertebrates, is an essential and specific component of the receptor for HTLV. Moreover, interaction of GLUT-1 with the entire HTLV-1 and HTLV-2 envelopes as well as the truncated HTLV-1 and HTLV-2 RBDs alters glucose metabolism.

HTLV Envelopes Alter Lactate Metabolism

Cell proliferation in standard culture media is accompanied by acidification of the milieu that translates into a color change from red to yellow tones in the presence of the phenol-red pH indicator. Upon transfection of either highly syncytial HTLV-1 and HTLV-2 envelopes, or a non-syncytial chimeric envelope that harbors the HTLV-1 RBD in a MLV Env backbone ($H_{183}$FEnv), culture medium did not readily acidify, and harbored red tones for several days post-transfection (FIG. 1*a*). Moreover, expression of truncated soluble HTLV RBD proteins fused with either GFP, -HA, or -rFc tags also inhibited medium acidification. In contrast, no envelope construct that lacked HTLV RBD, including different MLV group envelopes, feline, porcine, lentiviral and Jaagsiekte retroviral Envs, as well as VSV-G and Ebola glycoproteins, had this effect. The lack of acidification associated with HTLV-1 or HTLV-2 Env expression was not an indirect consequence of their syncytial activity, since (i) medium acidification was observed in cells expressing a syncytial amphotropic-MLV Env (A-MLV devoid of the R peptide) (FIG. 1*a*) and (ii) medium acidification was blocked when HTLV Env was expressed in cells that are resistant to HTLV-Env mediated syncytia formation (NIH3T3 $TK^-$ cells)[Kim, 2003].

Decrease of pH in cell culture is primarily due to extracellular accumulation of lactate [Warburg, 1956]. Lactate is the major byproduct of anaerobic glycolysis in vitro and its excretion is mediated by an H+/lactate symporter [Halestrap, 1999]. We monitored lactate content in culture supernatants following transfection of various retroviral envelopes and RBD. Lactate accumulation was consistently 3-fold lower in $H_{183}$FEnv- and HTLV RBD-transfected cells than in control- or MLV Env-transfected cells (FIG. 1*b*). This decrease in extracellular glucose and fructose accumulation after HTLV RBD transfection was DNA dose-dependent. Moreover, we found that the decrease in lactate accumulation following transfection of HTLV RBD was apparent as early as 4 hours after the addition of fresh media (FIG. 1*c*).

Receptor Binding and Lactate Metabolism

To examine whether a direct relationship exists between binding of the HTLV envelope receptor and diminished extracellular acidification and lactate accumulation, we attempted to generate HTLV-1 RBD ($H1_{RBD}$) mutants with impaired receptor binding capacities. To this end, mutations resulting in single alanine substitutions were introduced at two different positions in $H1_{RBD}$, D106 and Y114 which are highly conserved among primate T-lymphotropic viruses. Although both D106A and Y114A RBD mutants were expressed and secreted as efficiently as the wild-type $H1_{RBD}$ (FIG. 3*a*), they exhibited significantly reduced (D106A) or non detectable (Y114A) binding to the HTLV receptor as detected by FACS analysis (FIG. 3*b*). Moreover, perturbations in lactate metabolism correlated with binding to the HTLV receptor: lactate accumulation was not reduced in cells expressing the non-binding Y114A RBD mutant and was minimally reduced in cells harboring the D106 RBD (FIG. 3*c*). Similar results were obtained with $H2_{RBD}$ harboring the same allelic mutations. These data favor a direct association between lactate-related metabolic alterations and HTLV Env receptor binding.

Extracellular lactate accumulates in cell cultures following its transport across cellular membranes by the MCT1 monocarboxylate transporter[Garcia, 1994]. Because HTLV and MLV share a common organization of the extracellular envelope [Kim, 2000] and the receptors for MLV Env are multi-spanning metabolite transporters [Overbaugh, 2001], we assessed whether the HTLV RBD bound to MCT1. Moreover, similar to our previous data concerning expression of the HTLV receptor on T cells [Manel, 2003], expression of MCT1 chaperone CD147 [Kirk, 2000] increases during T cell activation [Kasinrerk, 1992]. However, separate and combined overexpression of MCT1 and CD 147 did not result in increased $H1_{RBD}$ binding, arguing against a role for these molecules as receptors for HTLV Env.

HTLV Receptor and Glucose Metabolism

In addition to a decrease in extracellular lactate accumulation, expression of the HTLV RBD also led to decreased intracellular lactate content, indicative of metabolic alterations upstream of lactate transport. In cell cultures, lactate accumulation results from the degradation of glucose during anaerobic glycolysis. Therefore, we assessed whether the decreased accumulation of lactate observed upon expression of HTLV RBD was linked to glucose metabolism. We measured glucose consumption as normalized to cellular protein content. Glucose consumption of cells expressing an HTLV RBD within the context of the $H_{183}$FEnv entire envelope or the $H1_{RED}$ was significantly decreased as compared to control cells (FIG. 1*b*) and this defect was detectable as early as 8 hours post transfection. To determine if this decrease in glucose consumption corresponded to a decrease in glucose transport across cellular membrane, we measured 2-deoxyglucose and fructose uptake in control cells and cells expressing HTLV RBD (FIG. 1*c*). We observed that expression of either HTLV-1 or HTLV-2 RBD induced an approximately 4-fold decrease in 2-deoxyglucose uptake, while A-MLV RBD had only a minor effect. Inhibitors of glucose uptake, cytochalasin B and phloterin, also inhibited glucose uptake. Theses results were also true for 3-O-methylglucose transport. Fructose uptake in the same cells was not altered by the presence of HTLV-1 nor HTLV-2 RBD however A-MLV RBD induced a slight decreased. We next evaluated the effect of glucose deprivation on the availability of the HTLV receptor in both adherent human 293T cells and suspension Jurkat T cells. After overnight culture of cells in the absence of glucose, binding of $H1_{RBD}$ was consistently increased by 2-fold in both cell types (FIG. 1*d*). This effect of glucose deprivation was specific to HTLV as amphotropic MLV RBD ($A_{RBD}$) binding was only marginally affected (FIG. 1*d*). This phenomenon is reminiscent of a general metabolite transport feedback loop, whereby transporter availability at the cell surface increases upon substrate starvation [Martineau, 1972].

HTLV Envelopes Bind Glucose Transporter-1

A simple model whereby the HTLV envelope inhibits glucose consumption via direct binding to a glucose transporter can explain the metabolic effects described above. Upon evaluation of the different glucose transporter candidates, GLUT-1 appears to be the only one encompassing all the known properties of the HTLV receptor. Indeed, GLUT-1 expression is increased upon glucose deprivation and is transports glucose in all vertebrate cells [Mueckler, 1985], while fructose is transported by GLUT-5. Furthermore, GLUT-1 is not expressed on resting primary T cells and its expression is induced upon T cell activation [Rathmell, 2000; Chakrabarti, 1994] with kinetics that are strikingly similar to what we have reported for the HTLV receptor [Manel, 2003]. Since human but not murine erythrocytes have been described to be the cells exhibiting the highest concentration of GLUT-1[ Mueckler, 1994], we evaluated HTLV receptor availability on freshly isolated red blood cells. Binding of $H1_{RBD}$ on human erythrocytes was strikingly efficient, reaching levels higher than those observed on any other tested cell type, whereas $A_{RBD}$ binding to erythrocytes was minimal (FIG. 2*a*). On murine erythrocytes however, no significant $H1_{RBD}$ binding could be detected, despite a similar $A_{RBD}$ binding on murine and human erythrocytes. Furthermore, primary human hepatocytes do not express GLUT-1. Accordingly, we were unable to detecte $H1_{RED}$ binding to human primary hepatocytes, while $A_{RBD}$ binding could be readily detected.

In order to directly test the ability of HTLV envelopes to bind GLUT-1, we derived a tagged GLUT-1 expression vector and overexpressed this protein in HeLa cells. Both $H1_{RBD}$ and $H2_{RBD}$ binding was dramatically increased upon GLUT-1 overexpression (FIG. 4*b*). This interaction was specific as the HTLV-2 binding-defective mutant, D102A, as well as its HTLV-1 counterpart, D106A, did not bind GLUT-1 (FIG. 4*a*). Furthermore, $H1_{RBD}$ and $H2_{RBD}$ binding remained at background levels upon overexpression of the amphotropic MLV envelope receptor, the inorganic phosphate transporter PiT2 [Miller, 1994]. Conversely, binding of $A_{RBD}$ was not increased after GLUT-1 overexpression but as expected, this interaction was increased upon transfection of PiT2 (FIG. 4*a*). GLUT-3 is the closest isoform to GLUT-1, and transports glucose with kinetics similar to that of GLUT-1. Thus, we derived a tagged GLUT-3 expression vector. Albeit similar overexpression levels of GLUT-1 and GLUT-3 in 293T cells, GLUT-3 did not induce any increase in $H1_{RBD}$ binding (FIG. 4*b*), suggesting that increase $H1_{RED}$ binding in cells overexpressing GLUT-1 is not an indirect consequence of increased glucose uptake. To determine if GLUT-1 transfected cells were directly responsible for the observed increased in $H1_{RBD}$binding, we derived fluorescent tagged GLUT-1 and GLUT-3 to unequivocally identify GLUT-overexpressing cells in the course of our FACS analysis. In this context, only cells overexpressing GLUT-1-DsRed2 displayed an significant increase in $HI_{RED}$ binding, while overexpressing GLUT-3-DsRed2 had no effect on $H1_{RBD}$ binding. Consequently, we tested if HTLV glycoproteins directly interacts with GLUT-1 proteins. To this end, we evaluated the ability of $H1_{RBD}$ to immunoprecipitate GLUT-1. As shown n fig is in FIG. 4*c*, GLUT-1 could be readily detected upon immunoprecipitation with anti-rabbit-Fc-beads when it was co-expressed with H1$_{RBD}$, but could not be detected when expressed alone or with the H1$_{RBD}$ Y114A mutant. Moreover, a GFP-tagged HTLV-2 RBD colocalized with GLUT-1 but not with PiT2 as assessed by fluorescence microscopy. Therefore, the GLUT-1 glucose transporter is an essential component of the HTLV envelope receptor.

Interaction of GLUT-1 with its ligand cytochalasin B inhibits glucose transport [Kasahara, 1977]. Since we showed that binding of HTLV envelopes to GLUT-1 inhibits glucose consumption and uptake, we tested whether cytochalasin B would abrogate HTLV RBD binding. Indeed, cytochalasin B treatment of Jurkat T cells dramatically inhibited binding of H1$_{RBD}$, whereas binding of A$_{RBD}$ was not affected (FIG. 5a). Thus, GLUT-1 directed glucose transport as well as binding of HTLV envelopes to GLUT-1 are similarly inhibited by the cytochalasin B ligand. Altogether, these data demonstrate that GLUT-1 is a receptor for HTLV envelopes.

Figure 5:
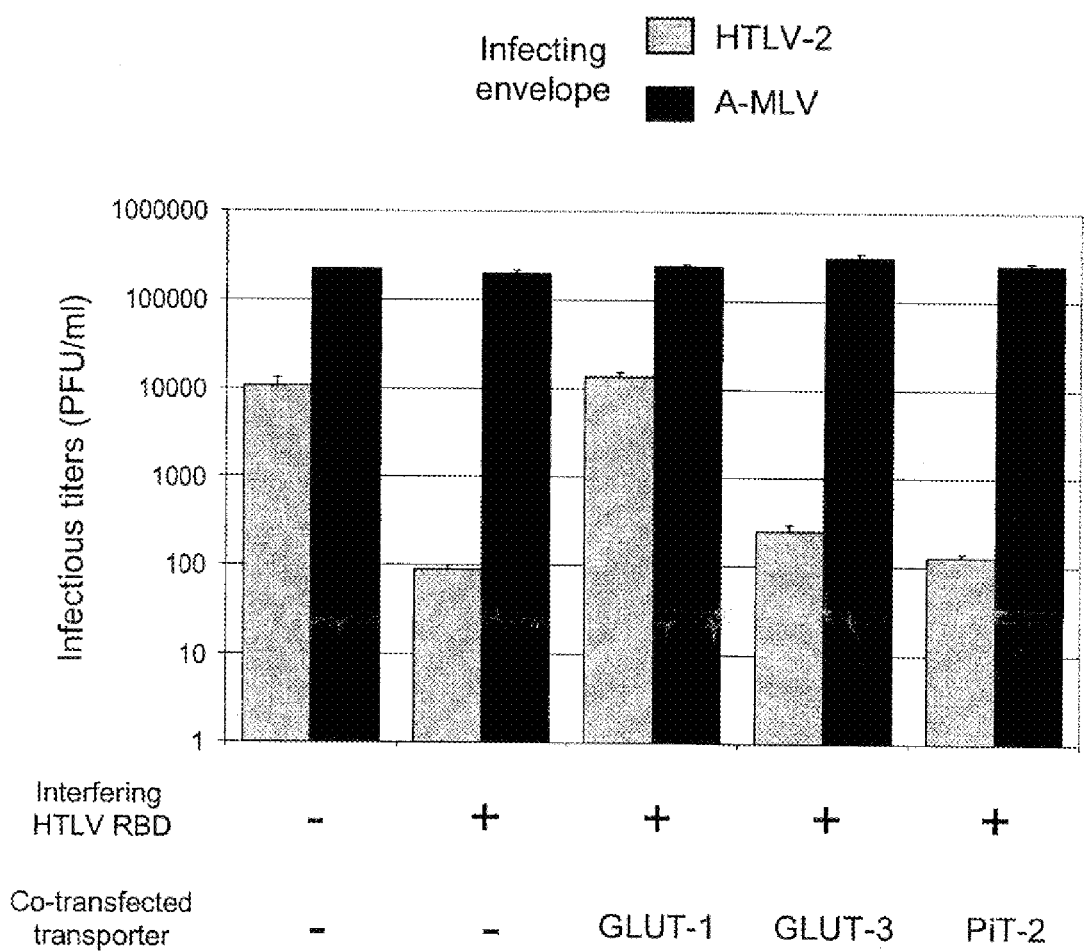

Viral receptor permits entry and thus infection. No cellular system currently exists that lacks GLUT-1 expression. Thus, we developed a system in which HTLV infection is specifically inhibited at the level of envelope-receptor interaction. In this system, overexpression of HTLV-2 RBD interferes with infecting incoming HTLV particles and specifically decreases HTLV titers by at least 2 logs, while no effect is detected on control AMLV titers. To determine if GLUT-1 is an entry receptor for HTLV, we overexpressed GLUT-1, GLUT-3 or Pit2 in addition to the interfering H2$_{RBD}$. While Pit2 and GLUT-3 had no effect on HTLV titers, GLUT-1 completely alleviated the interference to infection induced by H2$_{RBD}$ (FIG. 5). Interestingly, both GLUT-1 and GLUT-3, but not Pit2, alleviated the alteration of glucose metabolism induced by the HTLV RBD. Thus, GLUT-1 is an entry receptor for HTLV.

Discussion

Here we show that HTLV-1 and -2 envelopes interact with GLUT-1 through their receptor binding domains. This interaction strongly inhibits glucose consumption and glucose uptake, leading to decreased lactate production and a block in extracellular milieu acidification. Mutations that specifically altered receptor binding of both HTLV-1 and 2 envelopes released the block in glucose consumption, indicative of a direct correlation between receptor binding determinants in the HTLV envelopes and glucose transport. Glucose starvation was rapidly followed by increased binding of HTLV envelopes, highlighting a nutrient-sensing negative feedback loop between glucose availability and cell surface HTLV receptor expression. Further evidence converged to identify GLUT-1 as the receptor, including increased binding of HTLV RBD upon overexpression of GLUT-1 but not GLUT-3, immunoprecipitation of GLUT-1 by H1$_{RBD}$ but not the receptor-binding mutant H1$_{RBD}$ Y114A, uppermost binding of HTLV RBD on human erythrocytes, where GLUT-1 is the major glucose transporter isoform, and no binding of HTLV RBD on human primary hepatocytes and murine erythrocytes, where GLUT-1 is minimally expressed. Finally, GLUT-1 could specifically alleviate interference to infection induced by HTLV RBD. GLUT-1 fits all other known properties of the HTLV receptor. Indeed, as previously demonstrated for the HTLV receptor [Manel, 2003], GLUT-1, but not the GLUT 2-4 isoforms, is not expressed on resting T lymphocytes [Chakrabarti, 1994; Korgun, 2002] and is induced upon immunological [Frauwirth, 2002; Yu, 2003] or pharmacological [Chakrabarti, 1994] activation. Moreover, GLUT-1 orthologues are highly conserved among vertebrates, but are highly divergent between vertebrates and insects [Escher, 1999].

GLUT-1 is thus a new member of the multimembrane spanning metabolite transporters that serve as receptors for retroviral envelopes. Interestingly, until now, all envelopes that recognize these receptors have been encoded by retroviruses that have a so-called simple genetic organization, such as MLV, feline leukemia viruses, porcine endogenous retrovirus and the gibbon ape leukemia virus [Overbaugh, 2001], whereas HTLV belongs to the so-called complex retroviruses which code for several additional regulatory proteins. However, we have shown that in contrast to the wide phylogenetic divergence of their genomic RNA, the envelopes of HTLV and MLV share a similar modular organization with some highly conserved amino acid motifs in their respective receptor binding domains [Kim, 2000].

Cell-to-cell contact appears to be required for HTLV transmission, and the cytoskeleton appears to play a major role in this process [Igakura, 2003]. Indeed, we observed that the HTLV receptor, despite pancellular expression, is specifically concentrated to mobile membrane regions and cell-to-cell contact areas. It should therefore be expected that the HTLV envelope receptor is associated to the cytoskeleton. Importantly, a cytoplasmic-binding partner of GLUT-1, GLUT1CBP, which encodes a PDZ domain, has been reported to link GLUT-1 to the cytoskeleton [Bunn, 1999]. It will therefore be interesting to evaluate the respective roles of the HTLV envelope, its cytoskeleton-associated cellular partners, such as GLUT-1, GLUT1CBP and their immediate interacting cell components.

Because expression of the HTLV receptor is induced upon glucose starvation, transmission of HTLV may be more efficient in cells that are locally starved for glucose, such as lymphocytes in lymph nodes [Yu, 2003]. Furthermore, the ability of circulating erythrocytes to dock HTLV, as shown here, might provide a means to distribute HTLV to such tissues.

The identification of GLUT-1 as a receptor for HTLV envelopes provides additional clues as to the ubiquitous in vitro expression of the receptor on cell lines and the paradoxical restriction of HTLV tropism to T lymphocytes in vivo. Rapid and dramatic metabolic alterations associated with the blockade of glucose consumption are likely to take place upon expression of the HTLV envelope in vivo, early after infection. Therefore, we propose that in vivo, HTLV infection initially spreads with a large tropism, however early after infection the vast majority of cells that are highly dependent on GLUT-1 activity are rapidly eliminated. In contrast, resting T lymphocytes that have an extremely low metabolic rate and as such are much less dependent on glucose uptake, can tolerate this effect and are therefore maintained in vivo. Furthermore, local imbalances in the access to glucose following HTLV infection may lead to specific physiological alterations [Akaoka, 2001]. In this regard, it will be of interest to study the potential relationship between HTLV-associated neuropathologies and the specific dependence of neurons on GLUT-1 mediated glucose consumption [Siegel, 1998].

Methods.

Cell culture. 293T human embryonic kidney and HeLa cervical carcinoma cells were grown in Dulbecco's modified Eagle medium (DMEM) with high glucose (4.5 g/l) and Jurkat T-cells were grown in RPMI supplemented with 10% fetal bovine serum (FBS) at 37° C. in a 5% $CO_2$-95% air atmosphere. For glucose starvation experiments, cells were grown in either glucose-free DMEM (Life Technologies) or glucose-free RPMI—(Dutscher) with 10% dialyzed FBS (Life Technologies) and glucose (1 g/l) was supplemented when indicated.

Expression vectors. Full length envelope expression vectors for HTLV-1 (pCEL/2[Denesvre, 1995]) and Friend ecotropic MLV (pCEL/F [Denesvre, 1995]), have been previously described. For the HTLV-2 envelope, a fragment from pHTE2 [Rosenberg, 1998] encompassing the tax, rex and env genes and the 3' LTR was inserted in the pCSI [Battini, 1999] vector (pCSIX.H2). Full length envelope expression vectors for amphotropic MLV (pCSI.A), or devoid of its R peptide (pCSI.AΔR), and $H_{183}FEnv$ that contains the N-terminal 183 amino acids of the HTLV-1 receptor-binding domain in the F-MLV envelope background, as well as truncated envelope expression vectors, derived from pCSI and encoding either of the first 215 residues of HTLV-1 SU ($H1_{RBD}$), the first 178 residues of HTLV2-SU ($H2_{RBD}$) or the first 397 residues of the amphotropic murine leukemia virus (MLV) SU ($A_{RBD}$), fused to a C-terminal rabbit IgG Fc tag (rFc) or to EGFP ($H2_{RBD}$-GFP). All point mutations introduced in HTLV-1 and -2 RBD constructs were generated using the quickchange site-directed mutagenesis method and mutations were verified by sequencing. Human Glut-1 and Glut-3 cDNA were amplified by PCR from the pLib HeLa cDNA library (Clontech), and inserted into pCHIX, a modified version of the pCSI vector that contains a cassette comprising a factor Xa cleavage site, two copies of the hemagglutinin (HA) tag, and a histidine tag. The resulting construct (pCHIX.hGLUT1) encodes a GLUT-1 protein with a HA-His tag at the C-terminal end. GLUT-1 and GLUT-3 were also inserted in a modified pCSI vector containing a DsRed2 C-terminal tag. Similarly, human CD147 was amplified from 293T total RNA by RT-PCR and inserted into the pCHIX backbone in frame with the HA-His tag (pCHIX.hCD147).

Envelope expression and metabolic measurements. 293T cells were transfected with the various envelope expression vectors using a modified version of the calcium phosphate method. After an overnight transfection, cells were washed in phosphate-buffered saline (PBS) and fresh medium was added. Media were harvested at the indicated time points, filtered through a 0.45-μm pore-size filter, and lactate and glucose were measured with enzymatic diagnostic kits (Sigma). Values were normalized to cellular protein content using the Bradford assay (Sigma) after solubilization of cells in lysis buffer (50 mM Tris-HCl pH 8.0, 150 mM NaCl, 0.1% sodium dodecyl sulfate, 1.0% Nonidet P-40, 0.5% deoxycholate) and clarification by centrifugation.

Assay of hexose uptake. 2-deoxy-D[$1-^3H$]glucose, D[U-$^{14}C$]fructose and 3-O-[$^{14}C$]methyl-D-glucose were obtained from Amersham. Hexose uptake assay were adapted from Harrison et al (REF HARRISON 1991). After transfection, approximatively 250,000 were seeded/well in 24-well plates. The next day, cells were washed two times in PBS, incubated in serum-free DMEM, washed one time in serum-free glucose-free DMEM, and incubated for 20' in 500 μl serum-free glucose-free DMEM modulo inhibitors (20 μM cytochalasin B, 300 μM phloretin; SIGMA). Uptake was initiated by adding labeled hexoses to a final concentration of 0.1 mM (2 μCi/ml for 2-2-deoxy-D[$1-^3H$]glucose and 0.2 μCi/ml for D[U-$^{14}C$]fructose and 3-O-[$^{14}C$]methyl-D-glucose) and cells were incubated for 5' additional minutes. Cells were then resuspended in 500 μl cold serum-free glucose-free DMEM, wash one time in serum-free glucose-free DMEM, and solubilized in 400 μl of 0.1% SDS. 3 μl was used for Bradford normalization, while the rest was used for detection of either $^3H$ or $^{14}C$ by liquid scintillation in a Beckman counter.

Western blots. Culture media (10 μl) from 293T cells expressing wild type or mutant HTLV-1 RBDs, and/or GLUT-1 or GLUT-3 expression vecotor. were subjected to electrophoresis on SDS-15% acrylamide gels, transferred onto nitrocellulose (Protran; Schleicher & Schuell), blocked in PBS containing 5% powdered milk and 0.5% Tween 20, probed with either a 1:5000 dilution of horseradish peroxidase-conjugated anti-rabbit immunoglobulin or 1:2000 dilution of anti-HA 12CA5 (Roche) monoclonal antibody followed by a 1:5000 dilution of horseradish peroxidase-conjugated anti-mouse immunoglobulin, and visualized using an enhanced chemiluminescence kit (Amersham).

Binding assays. Binding assays were carried out as previously described [Manel, 2003]. Briefly, $5\times10^5$ cells (293T, HeLa, Jurkat or freshly isolated human erythrocytes) were incubated with 500 μl of $H^1RBD$, $H2_{RBD}$ or $A_{RBD}$ supernatants for 30 min at 37° C., washed with PBA (1% BSA, 0.1% sodium azide in PBS), and incubated with a sheep anti-rabbit IgG antibody conjugated to fluorescein isothiocyanate (Sigma). When indicated, cytochalasin B (20 μM; Sigma) was added to cells for 1 hour prior to binding analyses. Binding was analyzed on a FACSCalibur (Becton Dickinson) and data analysis was performed using CellQuest (Becton Dickinson) and WinMDI (Scripps) softwares.

Infections. 293T cells were transfected in 6-wells plate, and one day after transfection, medium was replaced by high glucose DMEM supplemented with fructose (5 g/l) and non-essential amino acids. The next day, infection was initiated by adding supernatants containing MLV particles pseuodtyped with either HTLV-2 or A-MLV envelopes. The following day, fresh medium was added, and 24 hours later cells were fixed and stained for alkaline phosphatase activity and dark focus of infection were counted. Viral particles were obtained by transfecting 293T cells with pLAPSN, pGagPoule and either pCSIX.H2 or pCSI.A, and harvesting the 0.45 μm-filtered supernatants 24 hours latter.

Figure Legends

Figure 1:
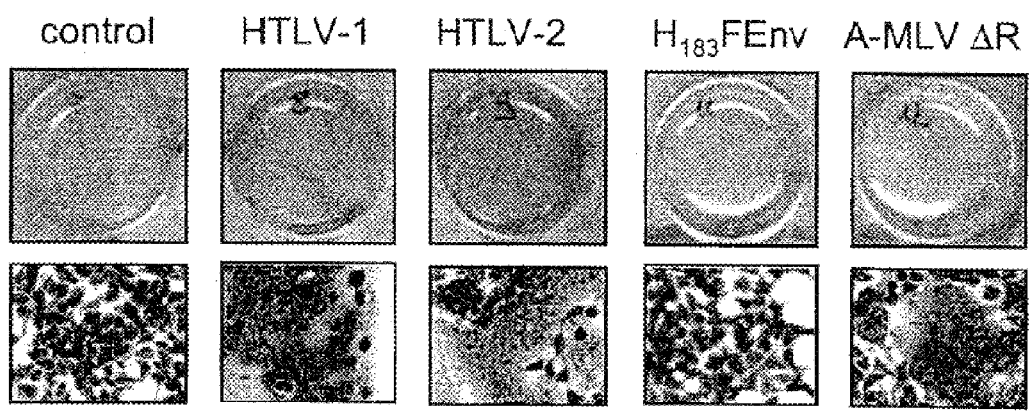
FIG. 1A is photographs of Medium acidification and syncytia formation in 293T cells one day post-transfection with control DNA or Env expression vectors, including syncytial wild-type HTLV-1 Env and HTLV-2 Env, a non-syncytial chimeric $H_{183}FEnv$, and syncytial A-MLV $\Delta R$ Env.
FIG. 1B illustrates the measurement of extracellular lactate and glucose in the culture medium of 293T cells two days following transfection with an irrelevant DNA (control), F-MLV Env, $H_{183}FEnv$, HTLV-1 RBD ($H1_{RBD}$) or amphotropic MLV RBD ($A_{RBD}$) expression vectors. Lactate and glucose concentrations were normalized to cellular protein content.
FIG. 1C illustrates the measurement of 2-deoxyglucose and fructose uptake following transfection of 293T with an irrelevant DNA (control), $H1_{RBD}$, $H2_{RBD}$ or $A_{RBD}$ expression vectors. Data are the means of triplicate measures and are representative of two to three independent experiments.
FIG. 1D illustrates the expression of the HTLV and amphotropic-MLV receptors on 293T and Jurkat T cells cultured overnight in the presence or absence of glucose, monitored by binding of $H1_{RBD}$ and $A_{RBD}$, respectively.
Figure 1B:
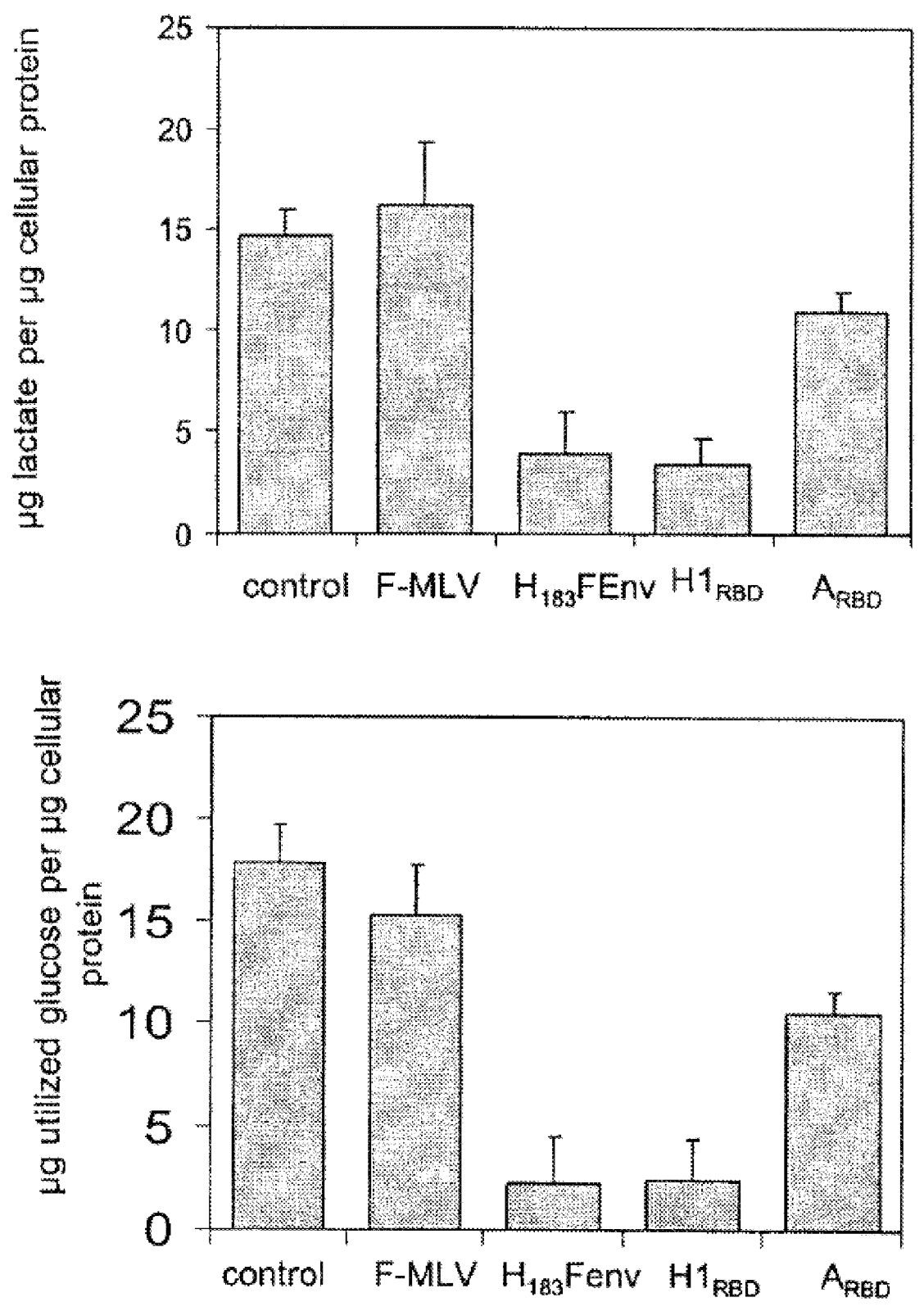
Figure 1:
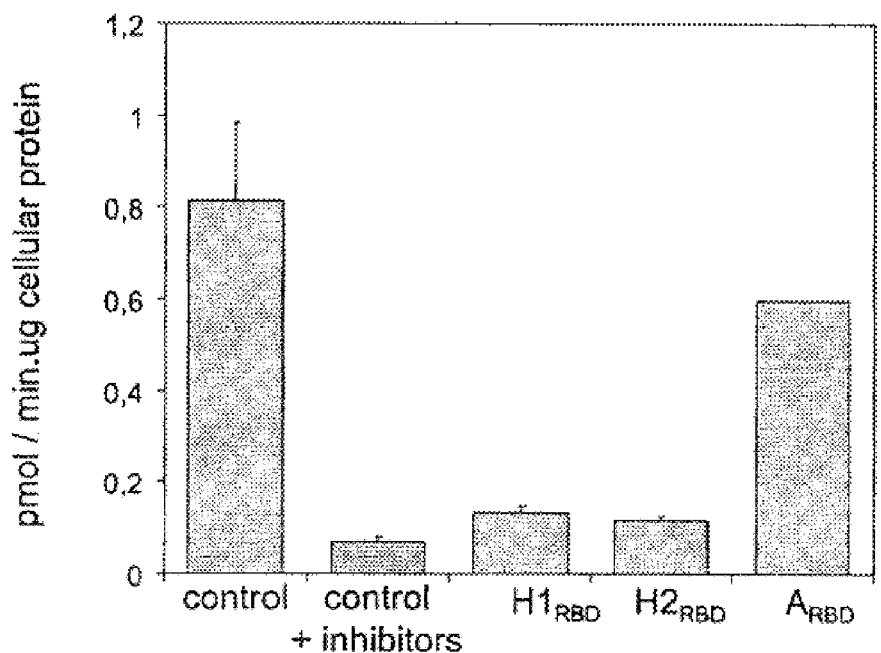
Figure 1:
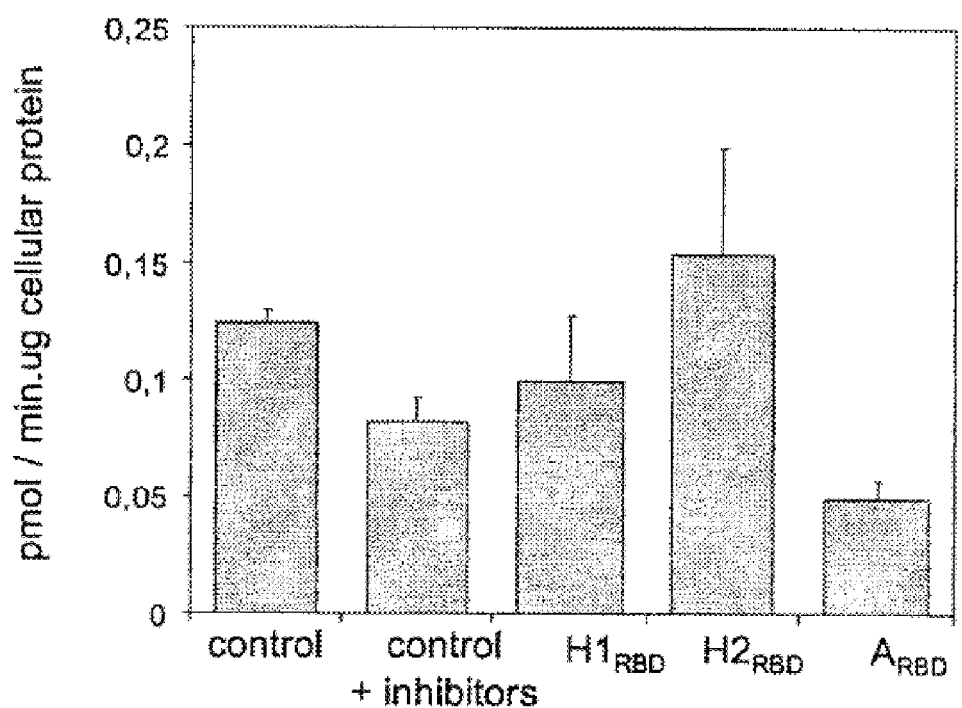

FIG. 1 Expression of the HTLV receptor-binding domain alters cellular metabolism. a, Medium acidification and syncytia formation in 293T cells one day post-transfection with control DNA or Env expression vectors, including syncytial wild-type HTLV-1 Env and HTLV-2 Env, a non-syncytial chimeric $H_{183}FEnv$, and syncytial A-MLV ΔR Env. b, Extracellular lactate and glucose in the culture medium of 293T cells were measured two days following transfection with an irrelevant DNA (control), F-MLV Env, $H_{183}FEnv$, HTLV-1 RBD ($H1_{RBD}$) or amphotropic MLV RBD ($A_{RBD}$) expression vectors. Lactate and glucose concentrations were normalized to cellular protein content. c, 2-deoxyglucose and fructose uptake following transfection of 293T with an irrelevant DNA (control), $H1_{RBD}$, $H2_{RBD}$ or $A_{RBD}$ expression vectors. Control cells were also incubated with glucose transporter inhibitors cytochalasin and phloretin. Data are the means of triplicate measures and are representative of two to three independent experiments. d, Expression of the HTLV and amphotropic-MLV receptors on 293T (1) and Jurkat T (2) cells cultured overnight in the presence or absence of glucose was monitored by binding of $H1_{RBD}$ and $A_{RBD}$, respectively.

Figure 2:
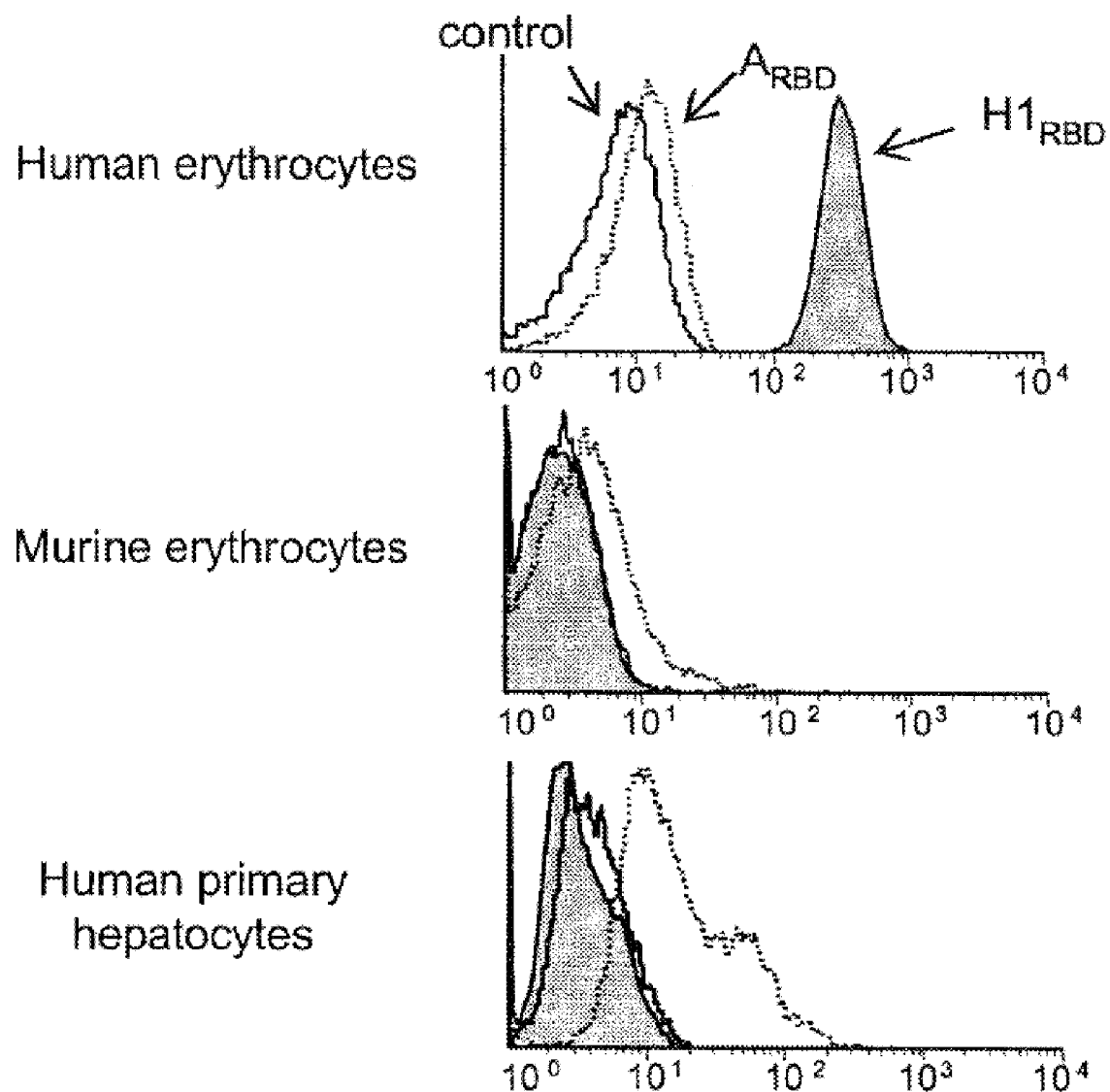
FIG. 2A illustrates the expression of the HTLV and amphotropic-MLV receptors at the surface of human and murine erythrocytes, as well as human primary hepatocytes.
FIG. 2B illustrates the binding $H1_{RBD}$ and $A_{RBD}$ to Jurkat cells in the absence or presence of the Glut-1 inhibitor cytochalasin B.

FIG. 2 HTLV receptor properties correlates with GLUT1 properties. a, Expression of the HTLV and amphotropic-MLV receptors at the surface of human and murine erythrocytes, as well as human primary hepatocytes. b, $H1_{RBD}$ and $A_{RBD}$ binding to Jurkat cells in the absence or presence of the Glut-1 inhibitor cytochalasin B.

Figure 3:
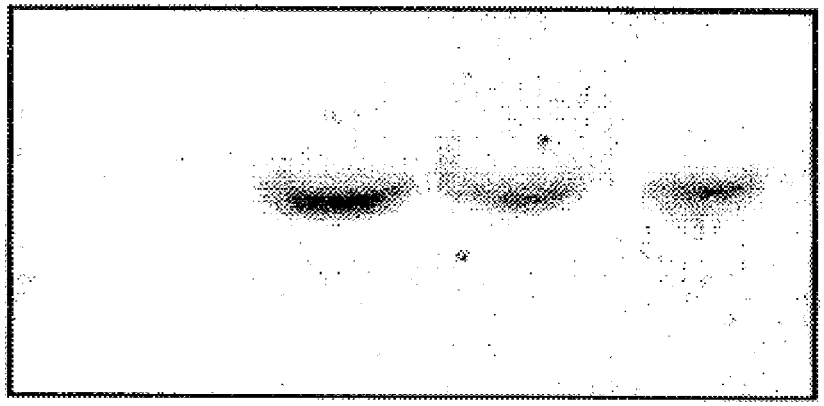
FIG. 3A is western blot analysis of the expression of $H1_{RBD}$ and the derived mutants D106A and Y114A in the supernatant of 293T cells following transfection with the various expression plasmids.

FIG. 3B illustrates the binding of $H1_{RBD}$ and the D106A and Y114A mutants to the HTLV receptor on HeLa cells.
Figure 3:
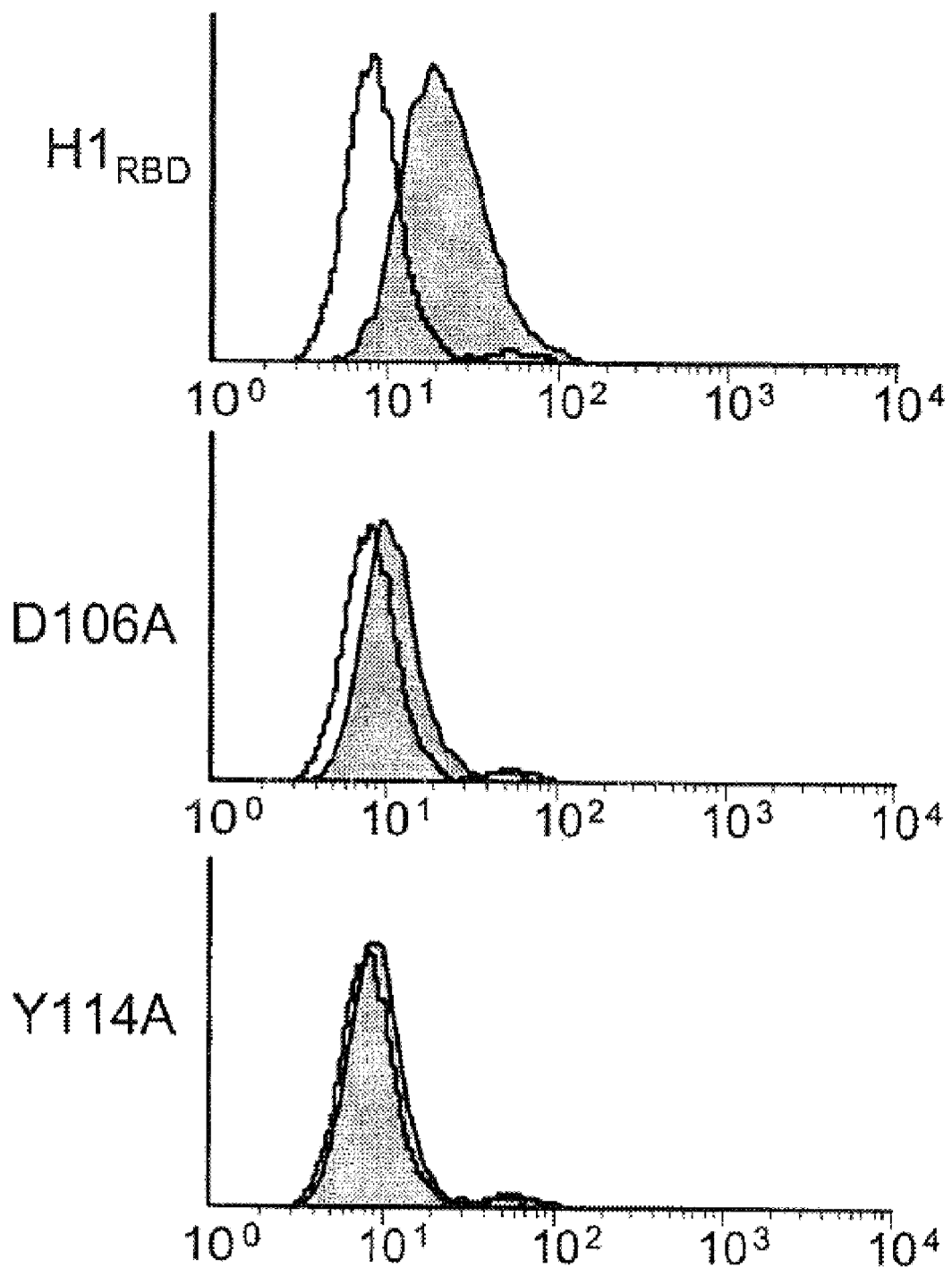
Figure 3:
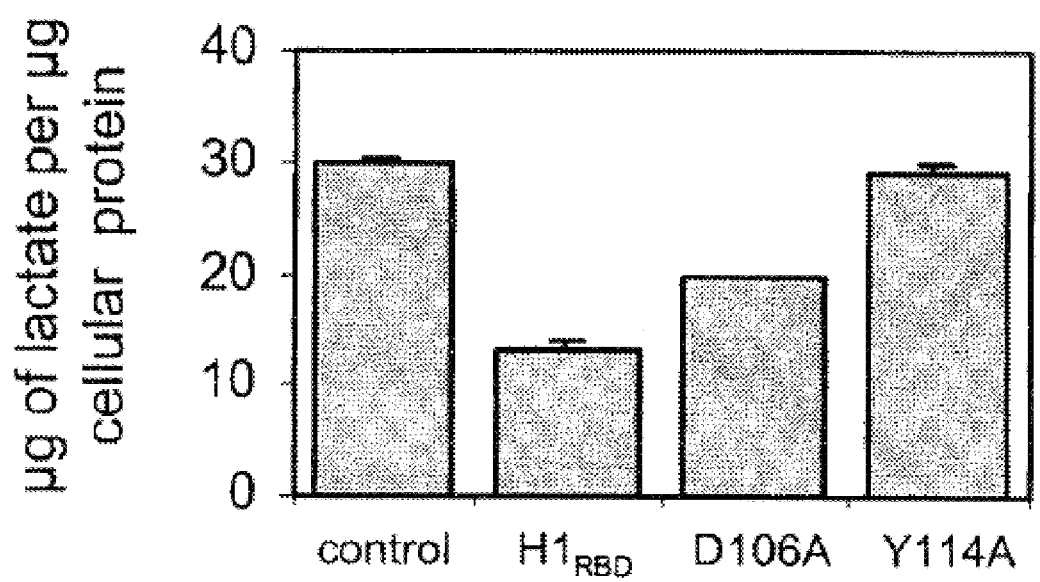

FIG. 3 HTLV receptor-binding correlates with altered lactate metabolism. a, Expression of $H1_{RBD}$ and the derived mutants D106A and Y114A was monitored by Western blot analysis of the supernatants of 293T cells following transfection with the various expression plasmids. b, Binding of $H1_{RBD}$ and the D106A and Y114A mutants to the HTLV receptor on HeLa cells. c, Extracellular lactate in the medium of 293T cells one day post transfection with an irrelevant DNA (control), H1$_{RBD}$ or the H1$_{RBD}$ D106A and Y114A mutants. Data are representative of three independent experiments.

Figure 4:
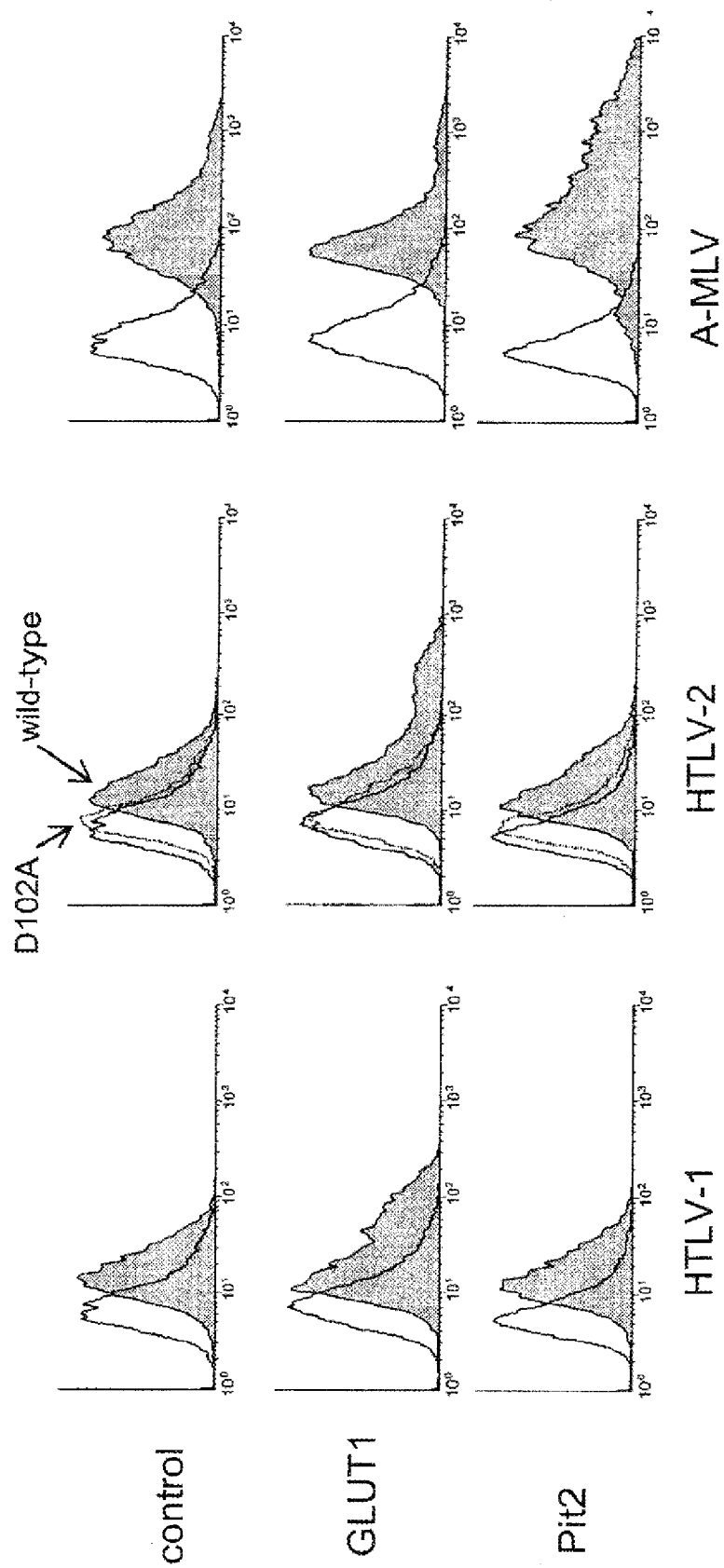
Figure 4:
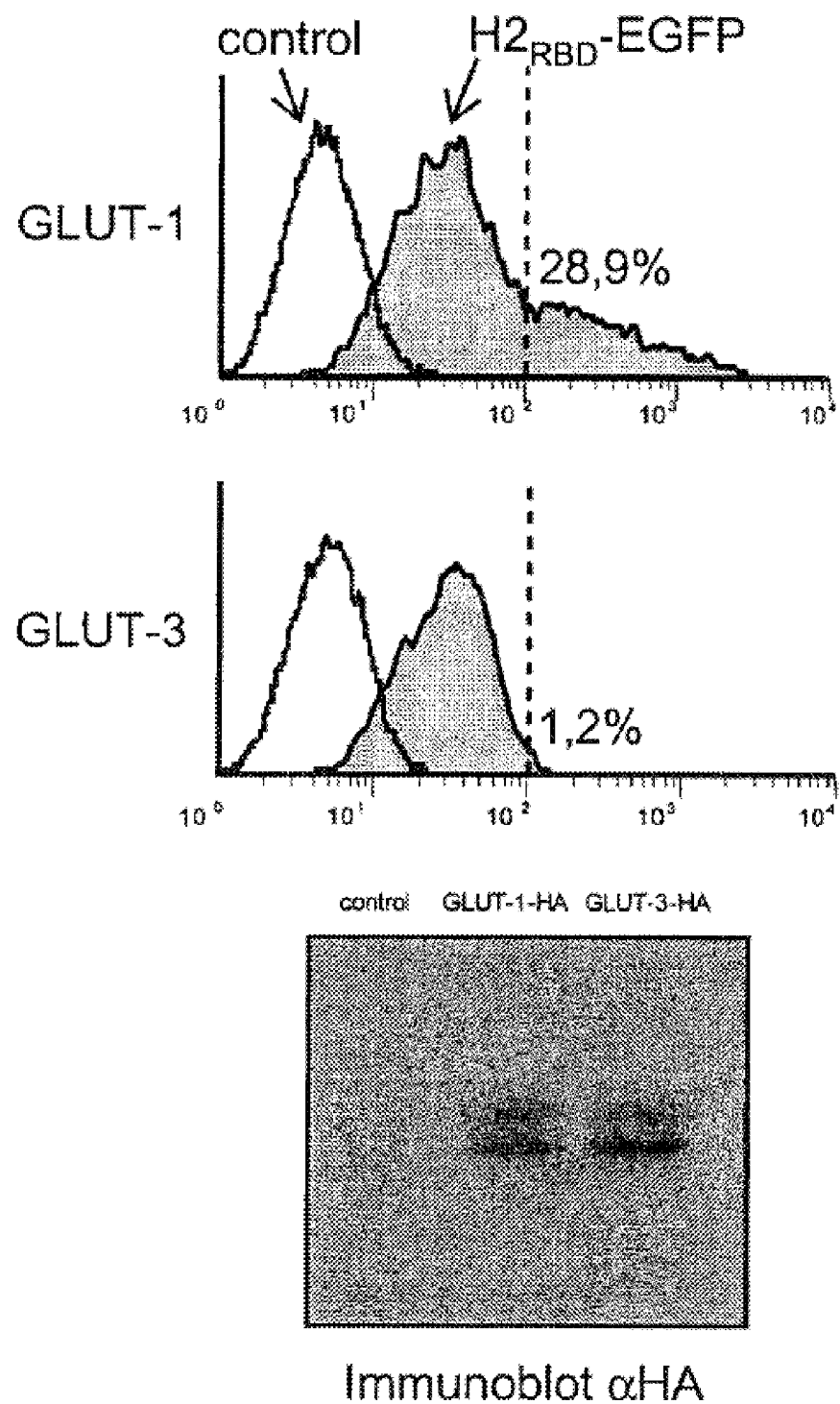
Figure 4:
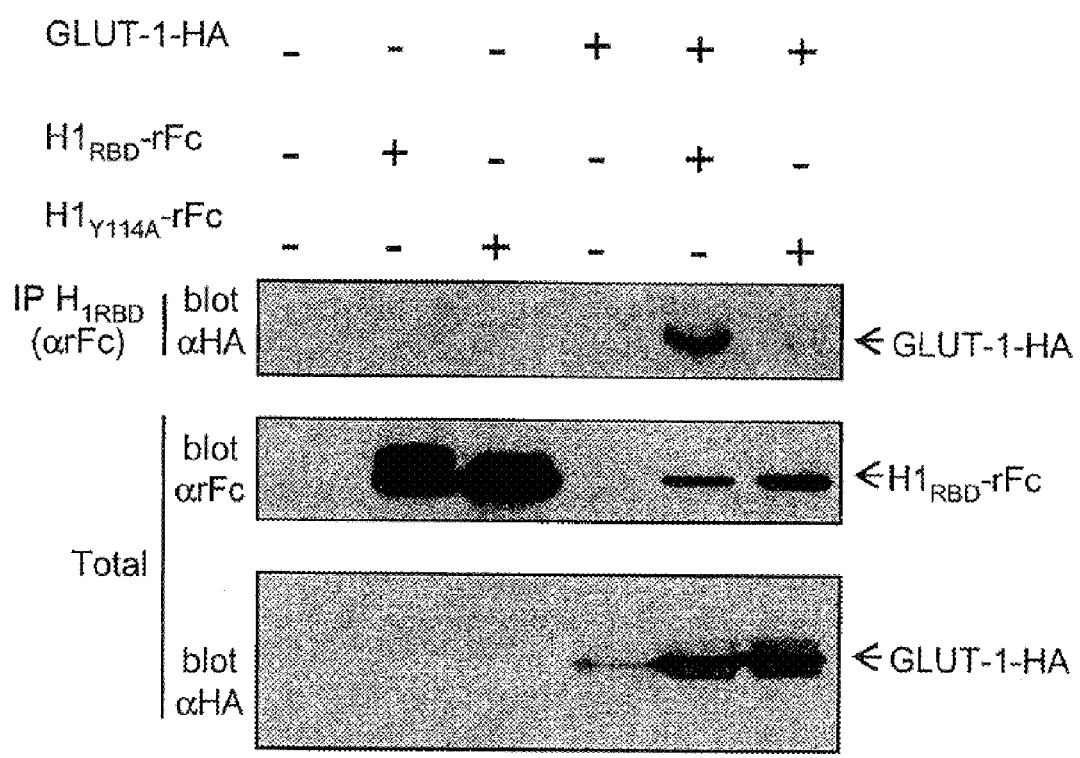

FIG. 4 GLUT-1 is a receptor for HTLV envelopes. a, Binding of H1$_{RBD}$, H2$_{RBD}$, H2$_{RBD}$ D102A mutant, and A$_{RBD}$ to control 293T cells or 293T cells overexpressing either GLUT-1 or PiT2. b, Binding of H2$_{RBD}$-EGFP to cells overexpressing GLUT-1-HA or GLUT-3-HA, and corresponding immuoblots using an anti-HA antibody. c, Immunprecipitation of GLUT-1-HA from 293T cells transfected with either an irrelevant construct, GLUT-1 alone, H1$_{RBD}$ alone, H1$_{RBD}$ Y114A alone, GLUT-1 with H1$_{RBD}$ or GLUT-1 with H1$_{RBD}$ Y114A expression vectors. Immunoprecipitation was performed using anti-rabbit-Fc beads and probed with an anti-HA antibody. Total cell extracts were blotted using an anti-rabbit Fc or an anti-HA antibody.

FIG. 5 GLUT-1 is an entry receptor for HTLV. Infections titer of MLV particles pseudotypes with HTLV-2 or A-MLV envelopes on 293T cells following transfection of an irrelevant or interfering $H2_{RBD}$ expression vectors alone or in addition to GLUT-1, GLUT-3 or Pit2 expression vectors.

1. Slattery, J. P., Franchini, G. & Gessain, A. Genomic evolution, patterns of global dissemination, and interspecies transmission of human and simian T-cell leukemia/lymphotropic viruses. *Genome Res* 9, 525-40. (1999).
2. Poiesz, B. J. et al. Detection and isolation of type C retrovirus particles from fresh and cultured lymphocytes of a patient with cutaneous T-cell lymphoma. *Proc Natl Acad Sci USA* 77, 7415-9. (1980).
3. Yoshida, M., Miyoshi, I. & Hinuma, Y. Isolation and characterization of retrovirus from cell lines of human adult T-cell leukemia and its implication in the disease. *Proc Natl Acad Sci USA* 79, 2031-5. (1982).
4. Gessain, A. et al. Antibodies to human T-lymphotropic virus type-I in patients with tropical spastic paraparesis. *Lancet* 2, 407-10. (1985).
5. Osame, M. et al. HTLV-I associated myelopathy, a new clinical entity. *Lancet* 1, 1031-2. (1986).
6. Cavrois, M., Gessain, A., Wain-Hobson, S. & Wattel, E. Proliferation of HTLV-1 infected circulating cells in vivo in all asymptomatic carriers and patients with TSP/HAM. *Oncogene* 12, 2419-23. (1996).
7. Hanon, E. et al. Fratricide among CD8(+) T lymphocytes naturally infected with human T cell lymphotropic virus type I. *Immunity* 13, 657-64. (2000).
8. Sutton, R. E. & Littman, D. R. Broad host range of human T-cell leukemia virus type 1 demonstrated with an improved pseudotyping system. *J Virol* 70, 7322-6. (1996).
9. Trejo, S. R. & Ratner, L. The HTLV receptor is a widely expressed protein. *Virology* 268, 41-8. (2000).
10. Kim, F. J., Manel, N., Boublik, Y., Battini, J. L. & Sitbon, M. Human T-cell leukemia virus type 1 envelope-mediated syncytium formation can be activated in resistant Mammalian cell lines by a carboxy-terminal truncation of the envelope cytoplasmic domain. *J Virol* 77, 963-9. (2003).
11. Berger, E. A., Murphy, P. M. & Farber, J. M. Chemokine receptors as HIV-1 coreceptors: roles in viral entry, tropism, and disease. *Annu Rev Immunol* 17, 657-700 (1999).
12. Clapham, P. R. & McKnight, A. HIV-1 receptors and cell tropism. *Br Med Bull* 58, 43-59 (2001).
13. Weiss, R. A. HIV receptors and cellular tropism. *IUBMB Life* 53, 201-5. (2002).
14. Niyogi, K. & Hildreth, J. E. Characterization of new syncytium-inhibiting monoclonal antibodies implicates lipid rafts in human T-cell leukemia virus type 1 syncytium formation. *J Virol* 75, 7351-61. (2001).
15. Daenke, S., McCracken, S. A. & Booth, S. Human T-cell leukaemia/lymphoma virus type 1 syncytium formation is regulated in a cell-specific manner by ICAM-1, ICAM-3 and VCAM-1 and can be inhibited by antibodies to integrin beta2 or beta7. *J Gen Virol* 80, 1429-36. (1999).
16. Hildreth, J. E., Subramanium, A. & Hampton, R. A. Human T-cell lymphotropic virus type 1 (HTLV-1)-induced syncytium formation mediated by vascular cell adhesion molecule-1: evidence for involvement of cell adhesion molecules in HTLV-1 biology. *J Virol* 71, 1173-80. (1997).
17. Denesvre, C. et al. TM domain swapping of murine leukemia virus and human T-cell leukemia virus envelopes confers different infectious abilities despite similar incorporation into virions. *J Virol* 70, 4380-6. (1996).
18. Daenke, S. & Booth, S. HTLV-1-induced cell fusion is limited at two distinct steps in the fusion pathway after receptor binding. *J Cell Sci* 113, 37-44 (2000).
19. Kim, F. J. et al. Definition of an amino-terminal domain of the human T-cell leukemia virus type 1 envelope surface unit that extends the fusogenic range of an ecotropic murine leukemia virus. *J Biol Chem* 275, 23417-20. (2000).
20. Jassal, S. R., Pohler, R. G. & Brighty, D. W. Human T-cell leukemia virus type 1 receptor expression among syncytium-resistant cell lines revealed by a novel surface glycoprotein-immunoadhesin. *J Virol* 75, 8317-28. (2001).
21. Hoshino, H., Shimoyama, M., Miwa, M. & Sugimura, T. Detection of lymphocytes producing a human retrovirus associated with adult T-cell leukemia by syncytia induction assay. *Proc Natl Acad Sci USA* 80, 7337-41. (1983).
22. Nagy, K., Clapham, P., Cheingsong-Popov, R. & Weiss, R. A. Human T-cell leukemia virus type I: induction of syncytia and inhibition by patients' sera. *Int J Cancer* 32, 321-8. (1983).
23. Kim, F. J., Manel, N., Garrido, E., Sitbon, M. & Battini, J. L. Truncated domains of the human T-cell leukemia virus envelope SU with receptor binding activity. *In preparation* (2003).
24. Manel, N. et al. The HTLV receptor is an early T-cell activation marker whose expression requires de novo protein synthesis. *Blood* 101, 1913-8. (2003).
25. Overbaugh, J., Miller, A. D. & Eiden, M. V. Receptors and entry cofactors for retroviruses include single and multiple transmembrane-spanning proteins as well as newly described glycophosphatidylinositol-anchored and secreted proteins. *Microbiol Mol Biol Rev* 65, 371-89, table of contents. (2001).
26. Warburg, O. On the origin of cancer cells. *Science* 123, 309-14. (1956).
27. Halestrap, A. P. & Price, N. T. The proton-linked monocarboxylate transporter (MCT) family: structure, function and regulation. *Biochem J* 343 Pt 2, 281-99. (1999).
28. Garcia, C. K., Goldstein, J. L., Pathak, R. K., Anderson, R. G. & Brown, M. S. Molecular characterization of a membrane transporter for lactate, pyruvate, and other monocarboxylates: implications for the Cori cycle. *Cell* 76, 865-73. (1994).
29. Kirk, P. et al. CD 147 is tightly associated with lactate transporters MCT1 and MCT4 and facilitates their cell surface expression. *Embo J* 19, 3896-904. (2000).
30. Kasinrerk, W. et al. Human leukocyte activation antigen M6, a member of the Ig superfamily, is the species homologue of rat OX-47, mouse basigin, and chicken HT7 molecule. *J Immunol* 149, 847-54. (1992).
31. Martineau, R., Kohlbacher, M., Shaw, S. N. & Amos, H. Enhancement of hexose entry into chick fibroblasts by starvation: differential effect on galactose and glucose. *Proc Natl Acad Sci USA* 69, 3407-11. (1972).
32. Mueckler, M. et al. Sequence and structure of a human glucose transporter. *Science* 229, 941-5. (1985).
33. Rathmell, J. C., Vander Heiden, M. G., Harris, M. H., Frauwirth, K. A. & Thompson, C. B. In the absence of extrinsic signals, nutrient utilization by lymphocytes is insufficient to maintain either cell size or viability. *Mol Cell* 6, 683-92. (2000).
34. Chakrabarti, R., Jung, C. Y., Lee, T. P., Liu, H. & Mookerjee, B. K. Changes in glucose transport and transporter isoforms during the activation of human peripheral blood lymphocytes by phytohemagglutinin. *J Immunol* 152, 2660-8. (1994).
35. Mueckler, M. Facilitative glucose transporters. *Eur J Biochem* 219, 713-25. (1994).
36. Miller, D. G., Edwards, R. H. & Miller, A. D. Cloning of the cellular receptor for amphotropic murine retroviruses reveals homology to that for gibbon ape leukemia virus. *Proc Natl Acad Sci USA* 91, 78-82. (1994).
37. Kasahara, M. & Hinkle, P. C. Reconstitution and purification of the D-glucose transporter from human erythrocytes. *J Biol Chem* 252, 7384-90. (1977).
38. Joost, H. G. & Thorens, B. The extended GLUT-family of sugar/polyol transport facilitators: nomenclature, sequence characteristics, and potential function of its novel members (review). *Mol Membr Biol* 18, 247-56. (2001).
39. Korgun, E. T. et al. Sustained hypoglycemia affects glucose transporter expression of human blood leukocytes. *Blood Cells Mol Dis* 28, 152-9. (2002).
40. Frauwirth, K. A. et al. The CD28 signaling pathway regulates glucose metabolism. *Immunity* 16, 769-77. (2002).
41. Yu, Q., Erman, B., Bhandoola, A., Sharrow, S. O. & Singer, A. In vitro evidence that cytokine receptor signals are required for differentiation of double positive thymocytes into functionally mature CD8(+) T cells. *J Exp Med* 197, 475-87. (2003).
42. Escher, S. A. & Rasmuson-Lestander, A. The Drosophila glucose transporter gene: cDNA sequence, phylogenetic comparisons, analysis of functional sites and secondary structures. *Hereditas* 130, 95-103 (1999).
43. Igakura, T. et al. Spread of HTLV-I Between Lymphocytes by Virus-Induced Polarization of the Cytoskeleton. *Science* 299, 1713-1716 (2003).
44. Bunn, R. C., Jensen, M. A. & Reed, B. C. Protein interactions with the glucose transporter binding protein GLUT1CBP that provide a link between GLUT1 and the cytoskeleton. *Mol Biol Cell* 10, 819-32. (1999).
45. Akaoka, H. et al. Functional changes in astrocytes by human T-lymphotropic virus type-1 T-lymphocytes. *Virus Res* 78, 57-66. (2001).
46. Siegel, G. J., Agranoff, B. W., Wayne Albers, W., Fisher, S. K. & Uhler, M. D. Circulation and Energy Metabolism of the Brain. *Basic Neurochemistry, Chapter* 5-31 (1998).
47. Denesvre, C., Sonigo, P., Corbin, A., Ellerbrok, H. & Sitbon, M. Influence of transmembrane domains on the fusogenic abilities of human and murine leukemia retrovirus envelopes. *J Virol* 69, 4149-57. (1995).
48. Rosenberg, A. R., Delamarre, L., Preira, A. & Dokhelar, M. C. Analysis of functional conservation in the surface and transmembrane glycoprotein subunits of human T-cell leukemia virus type 1 (HTLV-1) and HTLV-2. *J Virol* 72, 7609-14. (1998).
49. Battini, J. L., Rasko, J. E. & Miller, A. D. A human cell-surface receptor for xenotropic and polytropic murine leukemia viruses: possible role in G protein-coupled signal transduction. *Proc Natl Acad Sci USA* 96, 1385-90. (1999).
50. Rodrigues, P. & Heard, J. M. Modulation of phosphate uptake and amphotropic murine leukemia virus entry by posttranslational modifications of PIT-2. *J Virol* 73, 3789-99. (1999).

The invention claimed is:

1. A method for treating solid tumors overexpressing GLUT1 on cell surfaces, said method comprising administering to a subject in need thereof an effective amount of a GLUT1 binding polypeptide,
wherein,
said GLUT1 binding polypeptide comprises an envelope protein selected from the group consisting of HTLV-1, HTLV-2, STLV-1, STLV-2 or STLV-3, or a fragment thereof, wherein said fragment has an N-terminal located between positions 1 to 90, and a C-terminal located between positions 135 to 245, of the amino acid sequence of said envelope protein, and
said GLUT1 binding polypeptide or fragment thereof specifically binds to the ubiquitous vertebrate glucose transporter GLUT1 of SEQ ID NO: 2.

2. The method according to claim 1, wherein the solid tumors are selected from the group consisting of brain tumors, squamous cell carcinoma, hypopharyngeal carcinoma, breast cancer, cervical carcinoma, ovarian carcinoma, pancreatic cancer, and insulinoma.

3. The method of claim 1, wherein the GLUT1 binding polypeptide is able to bind to at least one fragment of GLUT1 selected from the group consisting of:

```
SEQ ID NO: 25:    NAPQKVIEEFY;
SEQ ID NO: 26:    NQTWVHRYGESILPTTLTTLWS;
SEQ ID NO: 27:    KSFEMLILGR;
SEQ ID NO: 28:    DSIMGNKDL;
SEQ ID NO: 29:    YSTSIFEKAGVQQP;
SEQ ID NO: 30:    EQLPWMSYLS;
SEQ ID NO: 31:    QYVEQLC;
and
SEQ ID NO: 32:    IVGMCFQYVEQLC.
```

4. The method of claim 3, wherein the GLUT1 binding polypeptide is able to bind to

```
SEQ ID NO: 32:    IVGMCFQYVEQLC
```

5. The method of claim 1, wherein the GLUT1 binding polypeptide is a fragment of the envelope protein selected from the group consisting of:
an envelope protein of HTLV-1,
an envelope protein of HTLV-2,
an envelope protein of STLV-1,
an envelope protein of STLV-2, and
an envelope protein of STLV-3.

6. The method of claim 5, wherein the envelope protein is selected from the group consisting of: SEQ ID NO: 4, SEQ ID NO: 6, SEQ ID NO: 8, SEQ ID NO: 10, and SEQ ID NO: 12.

7. The method of claim 1, wherein said fragment has the N-terminal located between positions 75 to 90, and the C-terminal located between positions 135 to 150, of the amino acid sequence of said envelope proteins.

8. The method of claim 1, wherein the envelope protein sequence is selected from the group consisting of: SEQ ID NO: 4, SEQ ID NO: 6, SEQ ID NO: 8, SEQ ID NO: 10, and SEQ ID NO: 12.

9. The method of claim 1, wherein the envelope protein sequence is SEQ ID NO: 4, and the fragment has the N-terminal located between position 83 to 89, and the C-terminal located between position 139 to 145.

10. The method of claim 1, wherein the envelope protein sequence is SEQ ID NO: 6, and the fragment has the N-terminal located between position 79 to 85, and the C-terminal located between position 135 to 141.

11. The method of claim 1, wherein the envelope protein sequence is SEQ ID NO: 8, and the fragment has the N-terminal located between position 83 to 89, and the C-terminal located between position 139 to 145.

12. The method of claim 1, wherein the envelope protein sequence is SEQ ID NO: 10, and the fragment has the N-terminal located between position 79 to 85, and the C-terminal located between position 135 to 141.

13. The method of claim 1, wherein the envelope protein sequence is SEQ ID NO: 12, and the fragment has the N-terminal located between position 82 to 88, and the C-terminal located between position 138 to 144.

14. The method according to claim 1, wherein the solid tumor is breast cancer.

15. The method of claim 1, wherein said GLUT1 binding polypeptide comprises a fragment of the envelope protein of a human T-cell leukaemia virus (HTLV).

16. The method of claim 1, wherein said GLUT1 binding polypeptide comprises the polypeptide of SEQ ID NO: 6, or a fragment thereof that specifically binds to the GLUT1 of SEQ ID NO: 2.

17. A method of inhibiting glucose consumption in breast cancer tumor cells in a patient, comprising administering to the patient an effective amount of a GLUT1 binding polypeptide, said GLUT1 binding polypeptide comprising the polypeptide selected from the group consisting of: SEQ ID NO: 4, SEQ ID NO: 6, SEQ ID NO: 8, SEQ ID NO: 10, and SEQ ID NO: 12, or a fragment thereof that specifically binds to the GLUT1 of SEQ ID NO: 2.

18. A method of treating breast cancer, comprising administering to a patient in need thereof an effective amount of the polypeptide selected from the group consisting of: SEQ ID NO: 4, SEQ ID NO: 6, SEQ ID NO: 8, SEQ ID NO: 10, and SEQ ID NO: 12, or a fragment thereof that specifically binds to the GLUT1 of SEQ ID NO: 2, wherein the effective amount of the polypeptide inhibits glucose consumption of the breast cancer cells.

* * * * *